(12) United States Patent
Hirsch et al.

(10) Patent No.: US 8,741,584 B2
(45) Date of Patent: *Jun. 3, 2014

(54) FOLLISTATIN-LIKE PROTEIN-1 AS A BIOMARKER FOR INFLAMMATORY DISORDERS

(71) Applicant: University of Pittsburgh—of the Commonwealth System of Higher Education, Pittsburgh, PA (US)

(72) Inventors: Raphael Hirsch, Pittsburgh, PA (US); David C. Wilson, Monroeville, PA (US)

(73) Assignee: University of Pittsburgh—of the Commonwealth System of Higher Education, Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/758,405

(22) Filed: Feb. 4, 2013

(65) Prior Publication Data

US 2013/0149712 A1 Jun. 13, 2013

Related U.S. Application Data

(63) Continuation of application No. PCT/US2011/046742, filed on May 5, 2011.

(60) Provisional application No. 61/371,093, filed on Aug. 5, 2010, provisional application No. 61/371,090, filed on Aug. 5, 2010.

(51) Int. Cl.
*G01N 33/53* (2006.01)

(52) U.S. Cl.
USPC .......................................... 435/7.1; 435/7.2

(58) Field of Classification Search
None
See application file for complete search history.

(56) References Cited

U.S. PATENT DOCUMENTS

| | | |
|---|---|---|
| 4,946,778 A | 8/1990 | Ladner et al. |
| 5,143,854 A | 9/1992 | Pirrung et al. |
| 5,288,644 A | 2/1994 | Beavis et al. |
| 5,324,633 A | 6/1994 | Fodor et al. |
| 5,432,049 A | 7/1995 | Fischer et al. |
| 5,470,710 A | 11/1995 | Weiss et al. |
| 5,492,806 A | 2/1996 | Drmanac et al. |
| 5,503,980 A | 4/1996 | Cantor |
| 5,510,270 A | 4/1996 | Fodor et al. |
| 5,525,464 A | 6/1996 | Drmanac et al. |
| 5,547,839 A | 8/1996 | Dower et al. |
| 5,580,732 A | 12/1996 | Grossman et al. |
| 5,605,690 A | 2/1997 | Jacobs et al. |
| 5,661,028 A | 8/1997 | Foote |
| 5,800,992 A | 9/1998 | Fodor et al. |
| 6,410,232 B1 | 6/2002 | Holtzman |
| 7,972,599 B2 | 7/2011 | Hirsch et al. |
| 8,211,652 B2 | 7/2012 | Hirsch |
| 8,334,274 B2 | 12/2012 | Hirsch et al. |
| 2005/0202421 A1 | 9/2005 | Hirsch et al. |
| 2013/0011863 A1 | 1/2013 | Hirsch |

FOREIGN PATENT DOCUMENTS

| | | |
|---|---|---|
| EP | 0 373 203 | 6/1990 |
| EP | 0 785 280 | 7/1997 |
| WO | WO 94/06476 | 3/1994 |
| WO | WO 95/21265 | 8/1995 |
| WO | WO 96/31622 | 10/1996 |
| WO | WO 97/10365 | 3/1997 |
| WO | WO 97/27317 | 7/1997 |
| WO | WO 2004/018522 | 3/2004 |
| WO | WO 2005/005471 | 1/2005 |
| WO | WO 2005/032328 | 4/2005 |
| WO | WO 2009/097424 | 8/2009 |

OTHER PUBLICATIONS

Lara-Pezzi et al. (J. Mol. Cellular Cardiology 2007 vol. 42, p. S147).*
Widera et al. (Clinical Chem. 2009 vol. 55, p. 1794-1800).*
Oshima et al. (Circulation 2007 116, II-221 Abstract 1101).*
U.S. Appl. No. 12/864,709, Aug. 28, 2012 Certificate of Correction.
U.S. Appl. No. 12/864,709, Jul. 26, 2012 Request for Certificate of Correction.
U.S. Appl. No. 12/864,709, Jun. 13, 2012 Issue Notification.
U.S. Appl. No. 12/864,709, Jun. 4, 2012 Issue Fee payment.
U.S. Appl. No. 12/864,709, Mar. 2, 2012 Notice of Allowance.
U.S. Appl. No. 12/864,709, Feb. 17, 2012 Response to Non-Final Office Action.
U.S. Appl. No. 12/864,709, Nov. 17, 2011 Non-Final Office Action.
U.S. Appl. No. 12/864,709, Sep. 27, 2011 Response to Non-Final Office Action.
U.S. Appl. No. 12/864,709, Apr. 27, 2011 Non-Final Office Action.
U.S. Appl. No. 13/538,918, Aug. 14, 2013 Non-Final Office Action.
U.S. Appl. No. 11/688,779, Feb. 19, 2013 Certificate of Correction.
U.S. Appl. No. 11/688,779, May 27, 2011 Issue Fee payment.
U.S. Appl. No. 11/688,779, Mar. 4, 2011 Notice of Allowance and Examiner Interview Summary.
U.S. Appl. No. 11/688,779, Dec. 2, 2010 Response to Non-Final Office Action.
U.S. Appl. No. 11/688,779, Sep. 2, 2010 Non-Final Office Action.
U.S. Appl. No. 11/688,779, Dec. 9, 2009 Amendment and Request for Continued Examination (RCE).

(Continued)

*Primary Examiner* — Jacob Cheu
(74) *Attorney, Agent, or Firm* — Baker Botts, LLP

(57) ABSTRACT

The present invention relates to methods and compositions for diagnosis of inflammatory disorders, and in non-limiting embodiments, of inflammatory disorders associated with elevated interleukin-1β ("IL-1β"), based on increased levels of follistatin-like protein 1 ("FSTL-1"). In particular non-limiting embodiments, the invention further provides for methods of identifying subjects with systemic onset juvenile idiopathic arthritis ("SOJIA") who are at increased risk for developing macrophage activation syndrome ("MAS") comprising detecting, in said subjects, hyper-increased levels of FSTL-1. In additional non-limiting embodiments, the invention provides for methods of identifying subjects with Kawasaki disease who are at increased risk of developing aortic aneurysms comprising detecting, in said subjects, hyper-increased levels of FSTL-1.

11 Claims, 11 Drawing Sheets

(56) References Cited

OTHER PUBLICATIONS

Figure 1A:
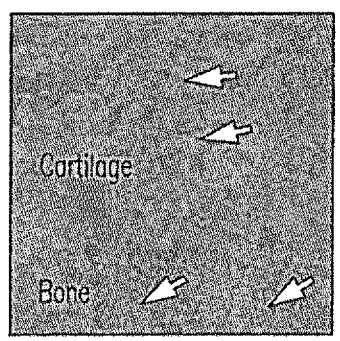

U.S. Appl. No. 11/688,779, Jul. 7, 2009 Final Office Action.
U.S. Appl. No. 11/688,779, Mar. 24, 2009 Response to Non-Final Office Action.
U.S. Appl. No. 11/688,779, Nov. 25, 2008 Non-Final Office Action.
U.S. Appl. No. 11/688,779, Jul. 31, 2008 Response to Restriction Requirement.
U.S. Appl. No. 11/688,779, May 1, 2008 Restriction Requirement.
U.S. Appl. No. 13/156,097, Nov. 12, 2012 Issue Fee payment.
U.S. Appl. No. 13/156,097, Oct. 22, 2012 Notice of Allowance.
U.S. Appl. No. 13/156,097, Sep. 17, 2012 Response to Non-Final Office Action.
U.S. Appl. No. 13/156,097, Jun. 15, 2012 Non-Final Office Action.
U.S. Appl. No. 13/156,097, May 16, 2012 Response to Restriction Requirement.
U.S. Appl. No. 13/156,097, Feb. 16, 2012 Restriction Requirement.
International Search Report and Written Opinion for PCT/US2011/046742, dated Apr. 6, 2012.
International Search Report for PCT/US2007/064441, dated Nov. 15, 2007.
International Search Report for PCT/US2009/032429, dated Jul. 13, 2009.
Atli, et al., "eNOS G894T polymorphism and abdominal aortic aneurysms", *Angiology*, 61(2):125-130 (2010).
Aggarwal, et al., "Interleukin-23 Promotes a Distinct CD4 T Cell Activation State Characterized by the Production of Interleukin-17", *The Journal of Biological Chemistry*, 278(3):1910-1914 (2003).
Beiser, et al., "A predictive instrument for coronary artery aneurysms in Kawasaki disease. US multicenter Kawasaki disease study group", *Am. J. Cardiol.*, 81(9):1116-1120 (1998).
Bettelli, et al., "Reciprocal Developmental Pathways for the Generation of Pathogenic Effector $T_H17$ and Regulatory T Cells", *Nature*, 441:235-238 (2006).
Bleesing et al., "The Diagnostic Significance of Soluble CD163 and Soluble Interleukin-2 Receptor α-Chain in Macrophage Activation Syndrome and Untreated New-Onset Systemic Juvenile Idiopathic Arthritis", *Arthritis and Rheumatism*, 56(3):965-971 (2007).
Bone, et al. (*Leadership Members of ACCP/SCCM*), "American College of Chest Physician/Society of Critical Care Medicine Consensus Conference: Definitions for sepsis and organ failure and guidelines for the use of innovative therapies in sepsis", *Critical Care Medicine*, 20(6):864-874 (1992).
Brown et al., "Control of I kappa B-alpha proteolysis by site-specific, signal-induced phosphorylation", *Science*. 267:1485-1488 (1995).
Burns, et al., "Kawasaki Syndrome", *Lancet*, 364(9433):533-544 (2004).
Chu et al., "IFNgamma deficient C57BL/6 (H-2b) mice develop collagen induced arthritis with predominant usage of T cell receptor πbeta6 and Vbeta8 in arthritic joints", *Annals of the Rheumatic Diseases*. 62:983-990 (2003).
Clutter et al., "Follistatin like protein-1 is a marker of inflammation", *The Journal of Immunology*, 178:131.31 (2007).
Clutter et al., "Follistatin-Like Protein 1 Promotes Arthritis by Up-Regulating IFN-$\gamma^1$", *The Journal of Immunology*, 182: 234-239 (2009).
Cole, et al., "The EBV-Hybridoma Technique and its Application to Human Lung Cancer", *Monoclonal Antibodies and Cancer Therapy*, pp. 77-96 (1985).
Constantinescu, et al., "Antibodies against IL-12 prevent superantigen-induced and spontaneous relapses of experimental autoimmune encephalomyelitis", *J Immunol.* 161:5097-104 (1998).
Cote, et al., "Generation of human monoclonal antibodies reactive with cellular antigens", *PNAS*, 80:2026-2030 (1983).
Current Protocols in Molecular Biology (F.M. Ausubel, et al., eds., 1987 including supplements through 2001). Table of contents.
Current Protocols in Nucleic Acid Chemistry, John Wiley & Sons, NY, 2000. Table of Contents retrieved on line from Wiley Online Library on Feb. 24, 2012 http://onlinelibrary.wiley.com/book/10.1002/0471142700/toc.

Diagnostic guidelines for Kawasaki disease. *Circulation*. 103(2):335-336 (2001).
Ehara et al., "Follistatin-related protein gene (FRP) is expressed in the synovial tissues of rheumatoid arthritis, but its polymorphisms are not associated with genetic susceptibility", *Clin Exp Rheumatol.* 22:707-712 (2004).
Fukazawa, et al., "Coronary artery aneurysm induced by Kawasaki disease in children show features typical senescence", *Circ. J.*, 71(5):709-715 (2007).
Galeotti, et al., "Kawasaki Disease: Aetiopathogenesis and therapeutic utility of intravenous immunoglobulin", *Autoimmun Rev.*, 9(6):441-448 (2010).
Genbank Accession No. BC000055 update Jul. 15, 2006, located at http://www.ncbi.nlm.nih.gov/entrez/viewer.fcqi?db=nuccore &id=33990756 last visited on Aug. 8, 2007, 4 pages.
Genbank Accession No. BC028921 updated Jul. 15, 2006, located at http://www.ncbi.nlm.gove/entrez/viewer.fcqi?db=nuccore& id=208100326 last visited Aug. 8, 2007, 3 pages.
Gett et al., "T cell fitness determined by signal strength", *Nat Immunol.* 4:355-360 (2003).
Gordon, et al., "When children with Kawasaki disease grow up myocardial and vascular complications in adulthood", *J. Am. Coll Cardiol.*, 54(21):1911-1920 (2009).
Hambrock, et al., "Structural Characterization of TSC-36/Flik", *Journal of Biological Chemistry*, 279:11727-11735 (2004).
Hardy et al., "Construction of adenovirus vectors through Crc-lox recombination", *J Virol.* 71(3):1842-1849 (1997).
Harlow and Lane (1988) Antibodies, a Laboratory Manual, Cold Spring Harbor Publications, NY. Table of contents.
Harlow and Lane (1999) Antibodies, a Laboratory Manual, Cold Spring Harbor Press, NY. (Beaucage, et al., eds). Table of contents.
Honorati, et al., "High in vivo expression of interleukin-17 receptor in synovial endothelial cells and chondrocytes from arthritis patients", *Rheumatology*, 40:522-527 (2001).
Hughes et al., "Induction of T helper cell hyporesponsiveness in an experimental model of autoimmunity using nonmitogenic anti-CD3 monoclonal antibody", *J. Immunol.* 153(7):3319-3325 (1994).
Hwang, et al., "IL-17 induces production of IL-6 and IL-8 in rheumatoid arthritis synovial fibroblasts via NF-κB- and P13-kinase/Akt-dependent pathways", *Arthritis Research & therapy*, 6(2):R120-R128 (2004).
Ivanov, et al., "The orphan nuclear receptor RORγt directs the differentiation program of proinflammatory IL-17$^+$ T helper cells", *Cell*, 126:1121-1133 (2006).
Iwasa, et al., "Selection of high-risk children for immunoglobulin therapy in Kawasaki disease", *Prog. Clin. Biol. Res.*, 250:543-544 (1987).
Johnston et al., "Regulation of a multigenic invasion programme by the transcription factor, AP-1:re-expression of a down-regulated gene, TSC-36, inhibits invasion", *Oncogene*. 19(47): 5348-58 (2000).
Kato, et al., "Long-term consequences of Kawasaki disease. A 10- to 21-year follow-up study of 594 patients", *Circulation*, 94(6):13 79-13 85 (1996).
Kawabata et al., "Ameliorative effects of follistatin-related protein/TSC-36/FSTL1 on joint inflammation in a mouse model of arthritis", *Arthritis Rheum*. 50(2):660-668 (2004).
Kawasaki, "Pediatric acute febrile mucocutaneous lymph node syndrom with characteristic desquamation of fingers and toes: my clinical observation of fifty cases", *Pediatr. Infect. Dis. J.*, 21(11:1-38 (2002).
Kelly, et al., "Recognition and Management of Macrophage Activation syndrome in Juvenile arthritis", *Curr. Opin. Rheumatol.*, 19(5):477-481 (2007).
Kim, et al., "Up-regulation of IL-23p19 expression in rheumatoid arthritis synovial fibroblasts by IL-17 through P13-kinase-,NF-κB- and p38 MAPK-dependent signalling pathways", *Rheumatology*, 46:57-64 (2007).
Kim et al., "TNF type 2 receptor (p75) lowers the threshold of T cell activation", *J. Immunol* 167(12):6812-6820 (2001).
Kohler, et al., "Continuous cultures of fused cells secreting antibody of predefined specificity", *Nature*, 256:495-497 (1975).

(56) References Cited

OTHER PUBLICATIONS

Kolls, et al., "Interleukin-17 family members and inflammation", *Immunity*, 21:467-476 (2004).

Koren, et al., "Kawasaki disease: Review of risk factors for coronary aneurysms", *J. Pediatr.*, 108(3):388-392 (1986).

Kotake, et al., "IL-17 in synovial fluids from patients with rheumatoid arthritis is a potent stimulator of osteoclastogenesis", *J. Clin. Invest.*, 103(9):1345-1352 (1999).

Kozbor, et al., "The production of monoclonal antibodies from human lymphocytes", *Immunology Today*, 4(3):72-79 (1983).

Kubo et al., "Characterization of a monoclonal antibody which detects all murine αβ T cell receptors", *J. Immunol.* 142(8):2736-2742 (1989).

Kwak et al., "Reciprocal cross-talk between RANKL and interferon-gamma-inducible protein 10 is responsible for bone-erosive experimental arthritis", *Arthritis Rheum.* 58(5):1332-1342 (2008).

Lara-Pezzi, et al., "Expression of follistatin-related genes is altered in heart failure", *Endocrinology*, 149(11):5822-5827 (2008).

Leonard, et al., "Prevention of experimental autoimmune encephalomyelitis by antibodies against interleukin 12", *J. Exp. Med.*, 181(1):381-386 (1995).

Lin, et al., "Cytokines predict coronary aneurysm formation in Kawasaki disease patients", *Eur. J. Pediatr.*, 152(4):309-312 (1993).

Lubberts, et al., "IL-1-independent role of IL-17 in synovial inflammation and joint destruction during collagen-induced arthritis", *J. Immunol.*, 167:1004-1013 (2001).

Mashimo, et al., "Decrease in the expression of a novel TGF β1-inducible and ras-recision gene, TSC-36, in human cancer cells", *Cancer Letters*. 113(1-2): 213-219 (1997).

Massague, et al., "Controlling TGF-beta signaling", *Genes Development*. 14(6):627-644 (2000).

The Merck Manuals Online Medical Library, [online]. Whitehouse Station, NJ: Merck Research Laboratories, 2006-2007 [retrieved on Nov. 19, 2007] Retrieved from the internet: <URL: http://www.merck.com/mmpe/print/sec06/ch068/ch068a.htlm>. Sepsis and Septic Shock, pp. 1-5.

Miyamae, et al., "Follistatin-like protein-1 is a novel proinflammatory molecule", *J Immunol.* 177(7):4758-4762 (2006).

Miyamae, et al., "682. Over-Expression of Follistatin-Like Protein Exacerbates Collagen Induced Arthritis", *Molecular Therapy*, 11:S264 (2005).

Mohan, et al., "Effect of cytokines and growth factors on the secretion of inhibin A. activin A and follistatin by term placental villous trophoblasts in culture", *European Journal of Endocrinology*, 145:505-511 (2001).

Molecular Cloning: A Laboratory Manual, Second Edition (Sambrook et al., 1989). Table of contents.

Molecular Cloning: A Laboratory Manual, Third Edition (Sambrook and Russel, 2001). Table of contents.

Morrison, et al., "Chimeric human antibody molecules: Mouse antigen-binding domains with human constant region domains", *PNAS*, 81:6851-6855 (1984).

Moustakas, "Smad signalling network", *J. Cell Sci.* 115(Pt. 17):3355-3356 (2002).

Nakae, et al., "Suppression of immune induction of collagen-induced arthritis in IL-17-deficient mice", *The Journal of Immunology*, 171:6173-6177 (2003).

Nakamura, et al., "Epidemiologic features of Kawasaki disease in Japan: Results of the 2007-2008 nationwide survey", *J. Epidemiol.*, 20(4):302-307 (2010).

Nakano, et al., "Scoring method for identifying patients with Kawasaki disease at high risk of coronary artery aneurysms", *Am. J. Cardiol.*, 58(9):739-742 (1986).

Negoro, et al., "Successful catheter interventional therapy for acute coronary syndrome secondary to Kawasaki disease in young adults", *Circ. J.*, 76(4):362-365 (2003).

Neuberger, et al., "Recombinant antibodies possessing novel effector functions", *Nature*, 312:604-608 (1984).

Newburger, et al., "The treatment of Kawasaki syndrome with intravenous gamma globulin", *the New England Journal of Medicine*, 315(6):341-347 (1986).

Ohashi et al., "TSC-36 (follistatin-related polypeptide) gene expression in estrogen receptor positive osteoblastic cell line, CDO7F", *Calcif Tissue Int.* 61(5): 400-403 (1997).

Okabayashi et al., "cDNA cloning and distribution of the *Xenopus* follistatin-related protein", *Biochem Biophys Res Commun.* 254(1): 42-48 (1999).

Oppmann, et al., "Novel p19 protein engages IL_12p40 to form a cytokine, IL-23, with biological activities similar as well as distinct from IL-12", *Immunity*, 13:715-725 (2000).

Oshima, et al., "Follistatin-like 1 is an Akt-regulated cardioprotective factor that is secreted by the heart", *Circulation*, 117(24):3099-3108 (2008).

Ouchi, et al., "Follistatin-like 1, a secreted muscle protein, promotes endothelial cell function and revascularization in ischemic tissue through a nitric-oxide synthase-dependent mechanism", *J. Biol. Chem.*, 283(47):32802-32811 (2008).

Overbergh, et al., "The use of real-time reverse transcriptase PCR for the quantification of cytokine gene expression", *Journal of Biomolecular Techniques*, 14:33-43 (2003).

PCR: The Polymerase Chain Reaction, (Mullis, et al., eds., 1994). Table of contents.

Pimiento, et al., "Endothelial nitric oxide synthase stimulates aneurysm growth in aged mice", *J. Vasc. Res.*, 45(3):251-258 (2008).

Printz, et al., "Noncoronary cardiac abnormalities are associated with coronary artery dilation and with laboratory inflammatory markers in acute Kawasaki disease", *J. Am. Coll. Cardiol.*, 57(1):86-92 (2011).

Ravelli, et al., "Preliminary Diagnostic guidelines for Macrophage Activation Syndrome Complicating systemic Juvenile Idiopathic Arthritis", *The Journal of Pediatrics*, 146:598-604 (2005).

Rowley, et al., "New developments in the search for the etiologic agent of Kawasaki disease", *Curr. Opin. Pediatr.*, 19(1):71-74 (2007).

Segal, et al., "An interleukin (IL)-10/IL-12 Immunoregulatory circuit controls susceptibility to autoimmune disease", *J. Exp. Med.*, 187(4):537-546 (1998).

Shibanuma et al., "Cloning from a mouse osteoblastic cell line of a set of transforming-growth-factor-beta 1-regulated genes, one of which seems to encode a follistatin-related polypeptide", *Eur J Biochemn.* 217(1):13-19 (1993).

Shin et al., "7,12-Dimethylbenz(a)Anthracene Treatment of a *c-rel* Mouse Mammary Tumor Cell Line Induces Epithelial to Mesenchymal Transition via Activation of Nuclear Factor-κB", *Cancer Res.* 66(5):2570-2575 (2006).

Simonini, et al., "Macrophage Activation Syndrome/ Hemophagocytic Lymphohistiocytosis and Kawasaki Disease", *Pediatr Blood Cancer*, 55:591 (2010).

Song, et al., "Risk factors for Kawasaki disease-associated coronary abnormalities differ depending on age", *Eur. J. Pediatr.*, 168(11):1315-1321 (2009).

Sowders et al., "Follistatin-like gene expression is upregulated in murine collagen induced arthritis", *FASEB Journal Fed. American Soc. For Experimental Biology*, 16(4):A326, (2002).

Standen, et al., "Septic Shock", *The New England Journal of Medicine*, 343(6):447-448 (2000).

Sudo et al., "In vitro differentiation and calcification in a new clonal osteogenic cell line derived from newborn mouse calvaria", *J. Cell Biol.* 96(1):191-198 (1983).

Sumitomo et al., "Expression of TGF-β1 inducible gene, TSc-36, causes growth inhibition in human lung cancer cell lines", *Cancer Letters*, 155(1): 37-46 (2000).

Suresh, et al., "Macrophage Activation Syndrome: a Rare complication of Incomplete Kawasaki Disease", *Annals of Tropical Pediatrics*, 3(0):61-64 (2010).

Takeda, et al., "Construction of chimaeric processed immunoglobulin genes containing mouse variable and human constant region sequences", *Nature*, 314:452-454 (1985).

Tamura, et al., "Endothelial damage due to impaired nitric oxide bioavailability triggers cerebral aneurysm formation in female rats", *J. Hypertens.*, 27(6):1284-1292 (2009).

(56) References Cited

OTHER PUBLICATIONS

Tanaka et al., "Cloning of follistatin-related protein as a novel autoantigen in systemic rheumatic diseases", *Int Immunol.* 10(9):1305-1314 (1998).

Tanaka et al., "Potential preventive effects of follistatin-related protein1TSC-36 on joint destruction and antagonistic modulation of its autoantibodies in rheumatoid arthritis", *Int Immunol.* 15(1):71-77 (2003).

Taubert, et al., "Nationwide survey of Kawasaki disease and acute rheumatic fever", *J. Pediatr.*, 119(2):279-282 (1991).

Terai, et al., "Prevalence of coronary artery abnormalities on Kawasaki disease is highly dependent on gamma globulin dose but independent of salicylate dose", *J. Pediatr.*, 131(6):888-893 (1997).

Thornton et al., "DNA microarray analysis reveals novel gene expression profiles in collagen-induced arthritis", *Clinical Immunology.* 105(2):155-168 (2002).

Thornton et al., "NK cells secrete high levels of IFN-gamma in response to in vivo administration of IL-2", *European Journal of Immunology.* 31(11):3355-3360 (2001).

Thornton et al., "Heterogeneous effects of IL-2 on collagen-induced arthritis", *J. Immunol.* 165(3):1557-1563 (2000).

Trojan et al., "Identification of metastasis-associated genes in prostate cancer by genetic profiling of human prostate cancer cell lines", *Anticancer Res.* 25(1A):183-191 (Jan.-Feb. 2005).

Yamada et al., "TNF:TNF-R T-Cell costimulatory pathways in transplantation", *Transplant Pnac.* 33(7-8):3070-3071 (2001).

van Stipdonk et al., "Dynamic programming of CD8$^+$ T lymphocyte responses", *Nat Immunol.* 4(4):361-365 (2003).

Veldhoen, et al., "TGFβ in the context of an inflammatory cytokine milieu supports de novo differentiation of IL-17-producing T cells", *Immunity*, 24:179-189 (2006).

Wilson, et al. "Follistatin-like Protein 1 is a Mesenchyme-Derived Inflammatory Protein and May Represent a Biomarker for Systemic-onset Juvenile Rheumatoid Arthritis", *Arthritis & Rheumatism*, 62(8): 2510-2516 (2010).

Yeo, et al., "Incomplete Kawasaki disease in patients younger than 1 year of age: A possible inherent risk factor", *Eur. J. Pediatr.*, 168(2):157-162 (2009).

Zhou, et al., "Identification of a follistatin-related protein from the tick *Haemaphysalis longicornis* and its effect on tick oviposition", *Gene*, 372:191-198 (2006).

\* cited by examiner

FOLLISTATIN-LIKE PROTEIN-1 AS A BIOMARKER FOR INFLAMMATORY DISORDERS

PRIORITY CLAIM

This application is a continuation of International Application Serial No. PCT/US2011/046742 filed Aug. 5, 2011 and claims priority to U.S. Provisional Application Ser. Nos. 61/371,093 and 61/371,090 both filed Aug. 5, 2010, the contents of all three of which are hereby incorporated by reference herein in their entireties.

GRANT INFORMATION

This invention was made with government support under grants RO1 AI073556, R01 AR056959, P30 AR047363, and AR052282 awarded by the National Institutes of Health. The government has certain rights in the invention.

1. INTRODUCTION

The present invention relates to methods and compositions for diagnosing inflammatory disorders, and particularly inflammatory disorders associated with elevated interleukin-1β ("IL-1β"), based on the serum and/or synovial fluid levels of follistatin-like protein-1 ("FSTL-1").

2. BACKGROUND OF THE INVENTION

2.1 IL-1β-Associated Disorders

Interleukin-1β ("IL-1β") is part of the eleven-member interleukin-1 superfamily of cytokines that operate in immunity and inflammation. IL-1β has been found to be elevated in a number of inflammatory conditions, and in particular in a relatively recently recognized group of disorders termed "autoinflammatory disorders" characterized by recurrent bouts of fever and systemic and/or local inflammation, which are often responsive to IL-1β blockade (see, for example, Dinarello, April 2011, Blood 117(14):3720-3732).

2.2 Juvenile Idiopathic Arthritis

Juvenile idiopathic arthritis ("JIA"), formerly known as juvenile rheumatoid arthritis (JRA), encompasses a heterogeneous group of diseases that are important causes of morbidity in children. JIA affects an estimated 250,000 children in the United States. The American College of Rheumatology (ACR) has classified JRA into a number of subtypes, including systemic-onset, polyarthritis, and oligoarthritis (Cassidy et al., 1986, Arthritis Rheum. 29(2):274-281). Each of these subtypes has a different clinical presentation, prognosis, and response to specific therapies, suggesting that they differ in their pathogenesis and pathophysiology. For instance, polyarticular JIA responds well to anti-TNF therapy (Lovell et al., 2000, N. Engl. J. Med. 342(11):763-769; Lovell et al., 2003, Arthritis Rheum 48(1):218-226) while systemic-onset JIA ("OJIA") does not (Horneff et al., 2004, Ann. Rheum. Dis. 63(12):1638-1644; Quartier et al., 2003, Arthritis Rheum. 48(4):1093-1101). Systemic-onset JIA also differs from the other forms of JIA in that the arthritis is often accompanied by fever, rash, organomegally, leukocytosis, and other systemic features in addition to arthritis. These systemic features can precede the development of arthritis by months or years, making the diagnosis at times difficult.

A number of biomarkers exist for aiding in the diagnoses and monitoring of rheumatoid arthritis (RA), including rheumatoid factor (Rose et al., 1948, Proc. Soc. Exp. Biol. Med. 68(1):1-6) and anti-citrullinated proteins ("CCP"; Sebbag et al., 1995, J. Clin. Invest. 95(6):2672-2679; Young et al., 1979, Br. Med. J. 2(61821:97-99). However, these markers are usually not present in JIA. The most commonly used biomarkers used in JIA include elevation in erythrocyte sedimentation rate ("ESR"), C-reactive protein ("CRP"), and platelet count, but these are non-specific.

2.3 Kawasaki Disease

Kawasaki disease (KD), an acute childhood vasculitis first described by Tomasaku Kawasaki in 1967 (Kawasaki, 1967, Arerugi 16(3):178-222), is the major cause of acquired cardiac disease in childhood (Taubert et al., 1991, J. Pediatr. 119(2):279-282). The etiology of KD remains unknown. It is believed that a possible undefined infectious agent triggers systemic inflammation and vasculitis in predisposed individuals (Galeotti et al., 2009, Autoimmun. Rev. 9(6):441-448; Rowley et al., 2007, Curr. Opin. Pediatr. 19(1):71-74). KD cases have been reported throughout the world, however there is a preponderance of expression of the disease among Asian populations and especially in Japan, where the incidence is increasing (Nakamura et al., 2010, J. Epidemiol. 20(4):302-307).

The major complication of KD is the development of coronary artery aneurysms (CAA). The incidence of CAA has decreased due to treatment with IVIG, however up to 5% of treated patients still develop aneurysms, as compared to up to 25% of untreated patients (Newburger et al., 1986, N. Engl. J. Med. 315(6:341-347; Burns et al., 2004, Lancet 364(9433): 533-544; Terai et al., 1997, J. Pediatr. 131(6):888-893; Kato et al., 1996, Circulation 94(6):1379-1385). Some cohort analyses have shown that Japanese male patients with known cardiovascular sequelae of childhood KD have a higher mortality ratio than other age-matched Japanese males (Gordon et al., 2009, J. Am. Coll. Cardio. 54(21): 1911-1920), and incidents of very early onset acute coronary syndrome in young adults believed to be secondary to KD have been reported (Negoro et al., 2003, Circ. J. 67(4):362-365).

2.4 FSTL-1

In an effort to identify novel biomarkers for JIA (and other forms of arthritis) gene expression was analyzed in the mouse model of collagen-induced arthritis (CIA) and it was discovered that a poorly characterized gene, follistatin-like protein 1 (FSTL-1), originally cloned from an osteoblast cell line as a TGF-β inducible gene (Shibanuma et al., 1993, Eur. J. Biochem. 217(11):13-19), was highly-overexpressed in mouse paws during early arthritis, especially at the interface of synovial pannus and eroding bone (Thornton et al., 2002, Clin. Immunol. 105(2):155-168). FSTL-1 was recognized as a biomarker of inflammation, including in the context of JIA and Kawasaki Disease (see United States Patent Application Publication No. 20110045507) and anti-FSTL-1 antibody has been shown to have beneficial effects in treating arthritis (see U.S. Pat. No. 7,972,599).

FSTL-1 is highly conserved across mammalian species. Human and mouse FSTL-1 share 92% identity in their amino acid sequence. FSTL-1 is secreted by cells of the mesenchymal lineage, including cardiac myocytes, and suppression of FSTL-1 expression by siRNA treatment leads to increased cardiomyocyte apoptosis (Oshima et al., 2008, Circulation 117(24):3099-3108). FSTL-1 has also been shown to have a role in promoting revascularization of skeletal muscle after ischemic injury (Ouchi et al., 2008, J. Biol. Chem. 283(47): 32802-32811). FSTL-1 expression has been found to be elevated in patients with heart failure but returns to normal levels upon recovery (Lara-Pezzi et al., 2008, Endocrinol. 149(11):5822-5827).

FSTL-1 has been found in RA synovial tissue (Clutter et al., 2009, J. Immunol. 182(1):234-239; Tanaka et al., 1998, Int. Immunol. 10(9):1305-1314) and anti-FSTL-1 antibodies have been detected in the serum and synovial fluid of RA patients (Tanaka et al., 1998, Int. Immunol. 10(9): 1305-1314). It was initially reported that administration of human FSTL-1 to Balb/c mice with antibody-induced arthritis ameliorated disease (Kawabata et al., 2004, Arthritis Rheum. 50(2):660-668), possibly by reducing synovial production of matrix metalloproteinases (Tanaka et al., 2003, Int. Immunol. 15(1):71-77). The effect was modest and it was subsequently demonstrated that FSTL-1 is a novel pro-inflammatory molecule with a previously unrecognized role in inflammation (Clutter et al., 2009, J. Immunol. 182(1):234-239; Myamae et al., 2006, J. Immunol. 177(7):4758-4762).

Transfection of FSTL-1 into macrophages and fibroblasts lead to up-regulation of proinflammatory cytokines felt to play central roles in chronic arthritis, including IL-1β and TNF-α Induction of FSTL-1 requires NFκB (Clutter et al., 2009, J. Immunol. 182(1):234-239). Over-expression of FSTL-1 in mouse paws by gene transfer resulted in severe paw swelling and arthritis, while neutralization of FSTL-1 suppressed arthritis (Clutter et al., 2009, J. Immunol. 182(1): 234-239). FSTL-1 was also found to be upregulated in the synovium of patients with RA, suggesting clinical relevance to our findings in the mouse model.

3. SUMMARY OF THE INVENTION

The present invention relates to methods and compositions for diagnosis of inflammatory disorders, and in non-limiting embodiments, of inflammatory disorders associated with elevated interleukin-β ("IL-1β"), based on increased levels of follistatin-like protein 1 ("FSTL-1"). In particular non-limiting embodiments, the invention further provides for methods of identifying subjects with systemic onset juvenile idiopathic arthritis ("SOJIA") who are at increased risk for developing macrophage activation syndrome ("MAS") comprising detecting, in said subjects, hyper-increased levels of FSTL-1. In additional non-limiting embodiments, the invention provides for methods of identifying subjects with Kawasaki disease who are at increased risk of developing aortic aneurysms comprising detecting, in said subjects, hyper-increased levels of FSTL-1.

4. BRIEF DESCRIPTION OF THE FIGURES

Figure 1B:
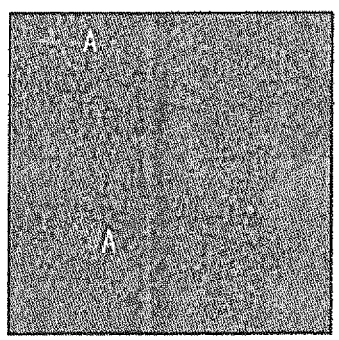
Figure 1C:
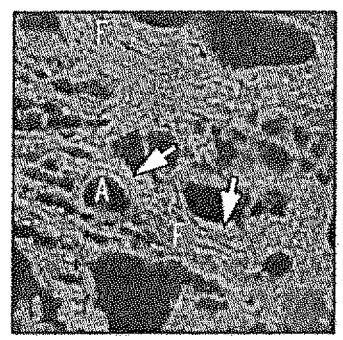

FIG. 1A-C. FSTL-1 is over-expressed in mesenchyme-derived tissues in CIA. FSTL-1 was visualized in knee joints from mice with CIA. (A) The bone-cartilage interface at high power, with the cartilage and bone visualized in phase contrast (red). Chondrocytes within amorphous matrix are seen in the upper part of the field; the cells label strongly for FSTL-1 (green; arrows). In the lower third of the field are osteocytes within the articular bone. These also label for FSTL-1 (arrows). The field shown is 100 μm square. (B) A high power field showing adipocytes (A) and fibroblast-like cells in synovial tissue. Anti-FSTL-1 antibody is labeled green; nuclei are visualized by Hoechst (blue fluorescence). The phase image is displayed in red with density inverted, so that the area of lipid, which is lost in processing, appear red. Field: 200 μm square. (C) FSTL-1 expression (green) in synovial fibroblasts (F) labeled with anti-CD90 (red); nuclei are blue. Note that many cells are labeled with both antibodies, and appear yellow (arrows). Adipocytes (A) appear as empty spaces; however, the phase image is inverted and merged as greyscale with the three colored fluorescent images. Field: 200 μm square.

FIG. 2A-D. FSTL-1 is induced by pro-inflammatory cytokines. The osteoblast cell line, MC3T3 (A), the adipocyte cell line, 3T3-L1, (B) and 2 RA fibroblast-like synoviocyte (FLS) cell lines (C, D) were cultured for 3 days in the presence or absence of TGF-β, IL-1β, TNF-α, or IL-6 and supernatants were assayed for FSTL-1. Each bar represents the mean and S.E.M. of 6 replicates. *p<0.05.

Figure 3:
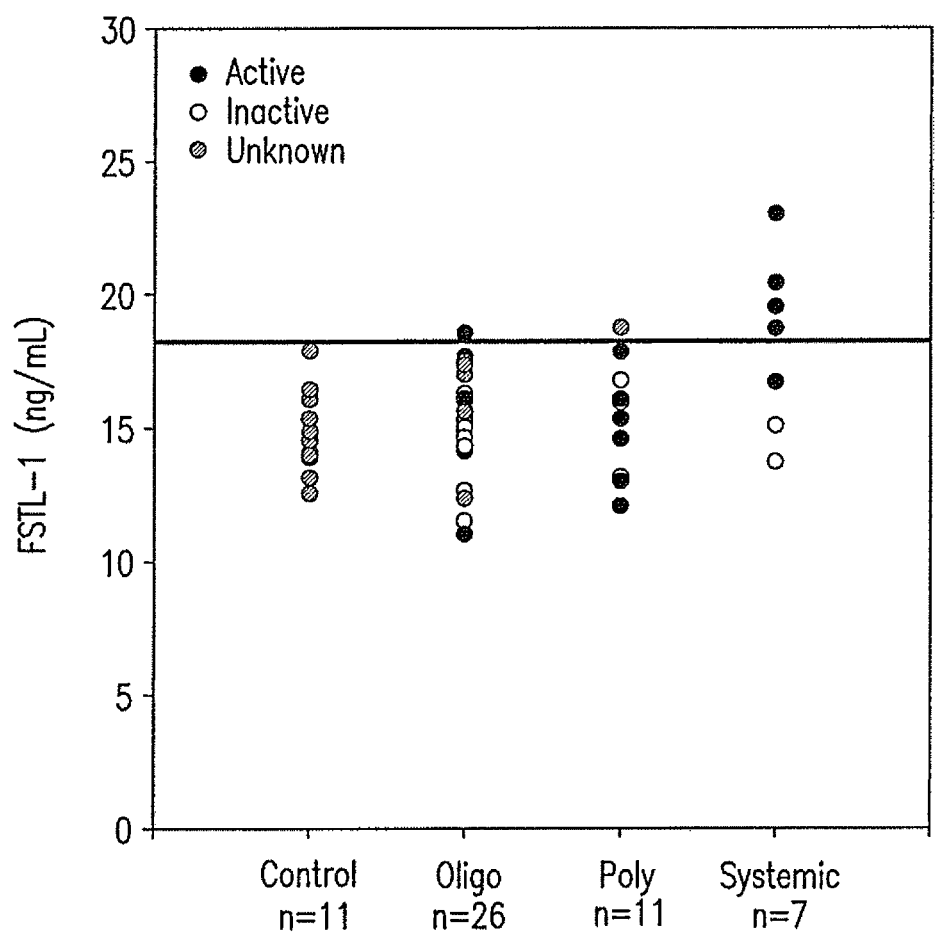

FIG. 3. FSTL-1 is elevated in sera of patients with active systemic-onset JRA. Sera from children with JRA, as well as pediatric control sera, were assayed for FSTL-1. Each circle represents an individual sample. Black circles indicate subjects with laboratory evidence of active disease (ESR≥20 mm/hr or a platelet count≥380×10$^9$/L). White circles indicate subjects with normal ESR and platelet count. Grey circles indicate subjects who did not have an ESR or platelet count. The horizontal line is drawn at a level of 18 ng/ml.

Figure 4:
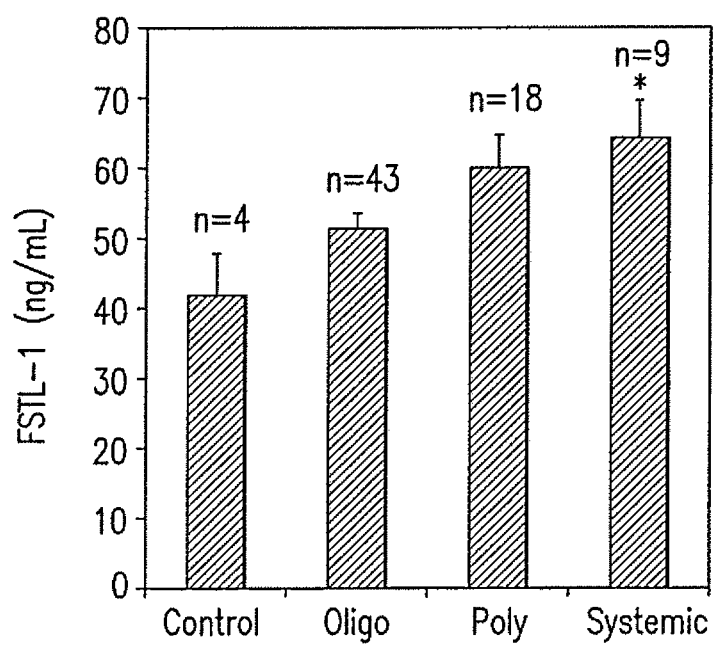

FIG. 4. FSTL-1 is elevated in synovial fluids of patients with systemic-onset JRA. Synovial fluids from children with JRA, as well as fluids from control subjects, were assayed for FSTL-1. Each bar represents the mean and S.E.M. of the indicated number of samples. *p<0.05 compared to controls.

Figure 5A:
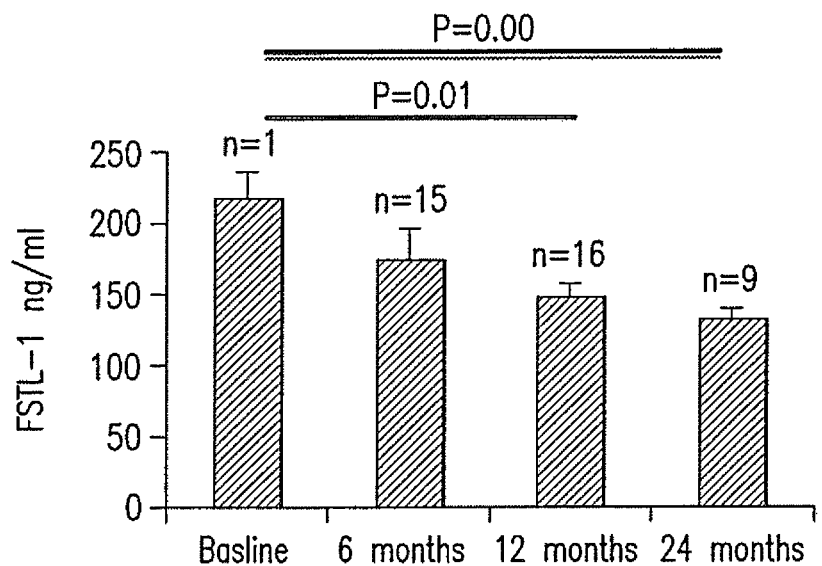
Figure 5B:
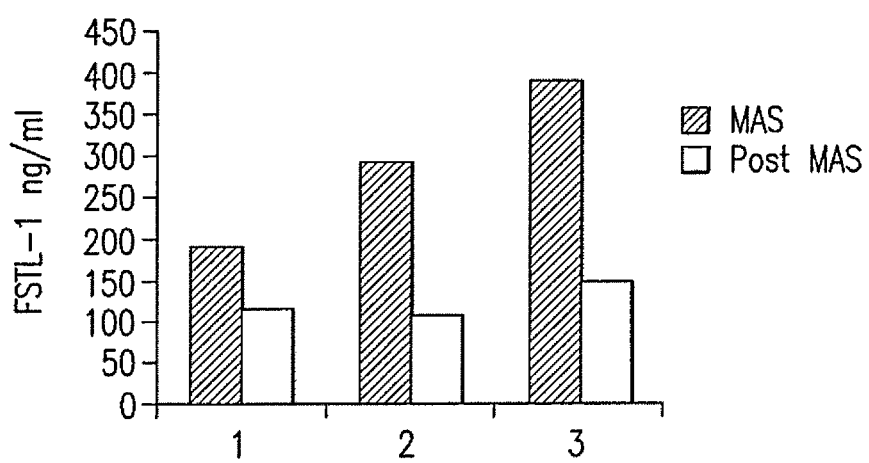

FIG. 5A-B. (A) FSTL-1 serum levels in SJIA over time (unpaired samples). (B) FSTL-1 serum levels pre- and post-MAS over time in 3 patients (paired samples).

Figure 6:
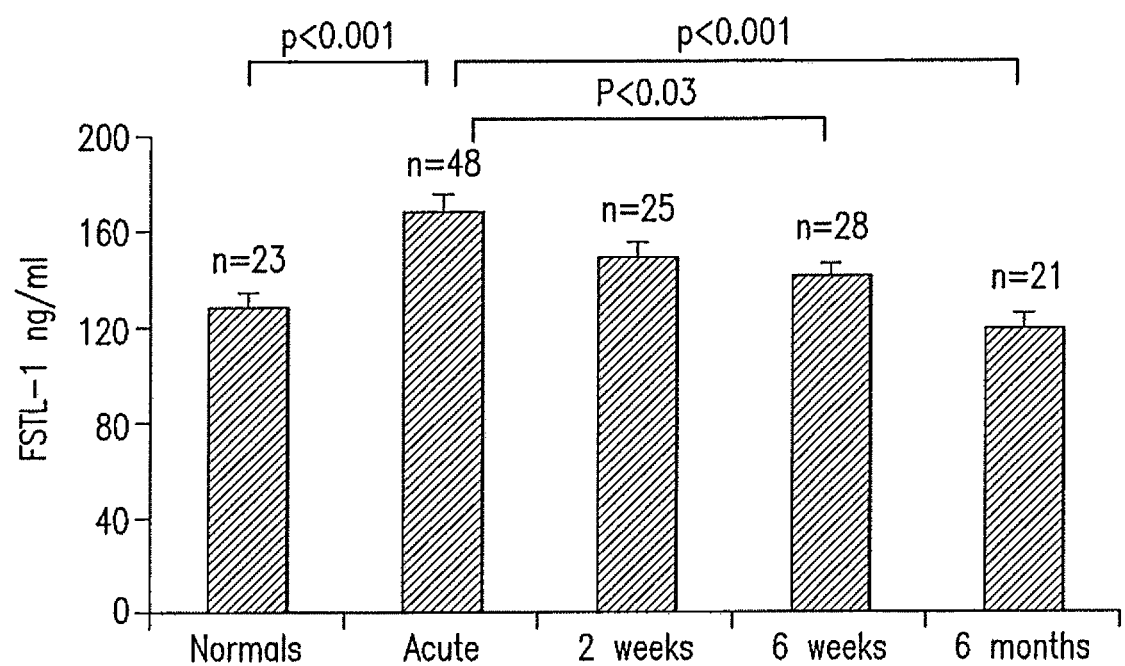

FIG. 6. FSTL-1 plasma levels in KD. Each bar represents the mean±SEM. n=number of patients.

Figure 7:
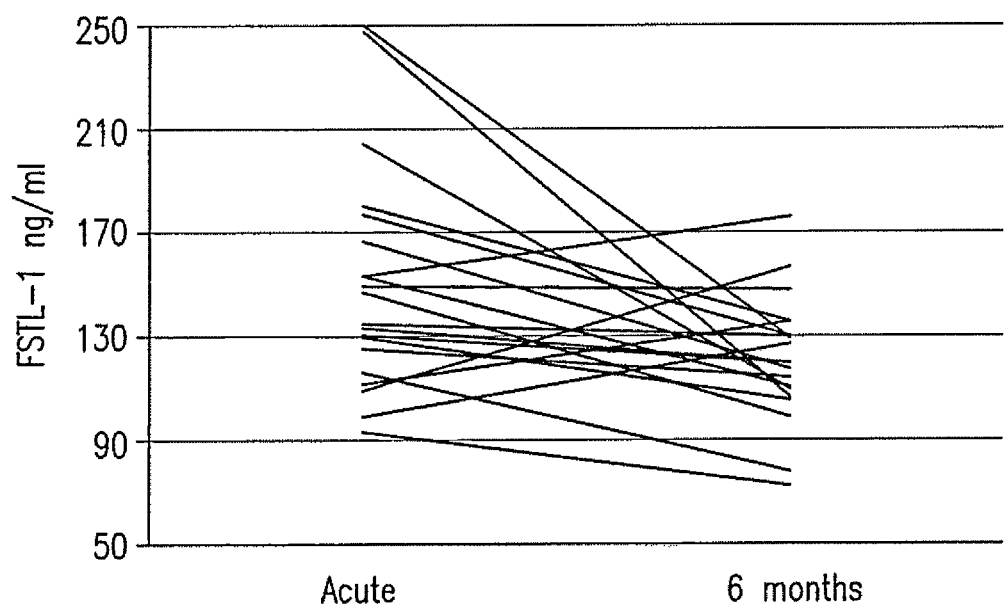

FIG. 7. Paired FSTL-1 plasma levels at presentation and after 6 months. Paired data was significantly different with p=0.012.

Figure 8:
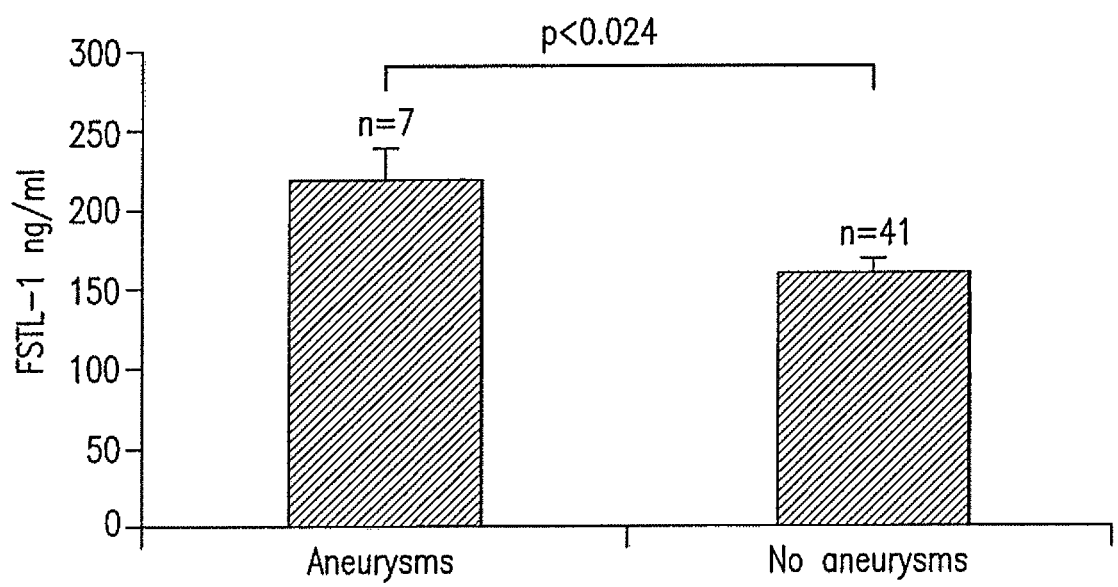

FIG. 8. Acute FSTL-1 plasma levels in patients with and without CAA. Each bar represents the mean±SEM. n=number of patients.

Figure 9:
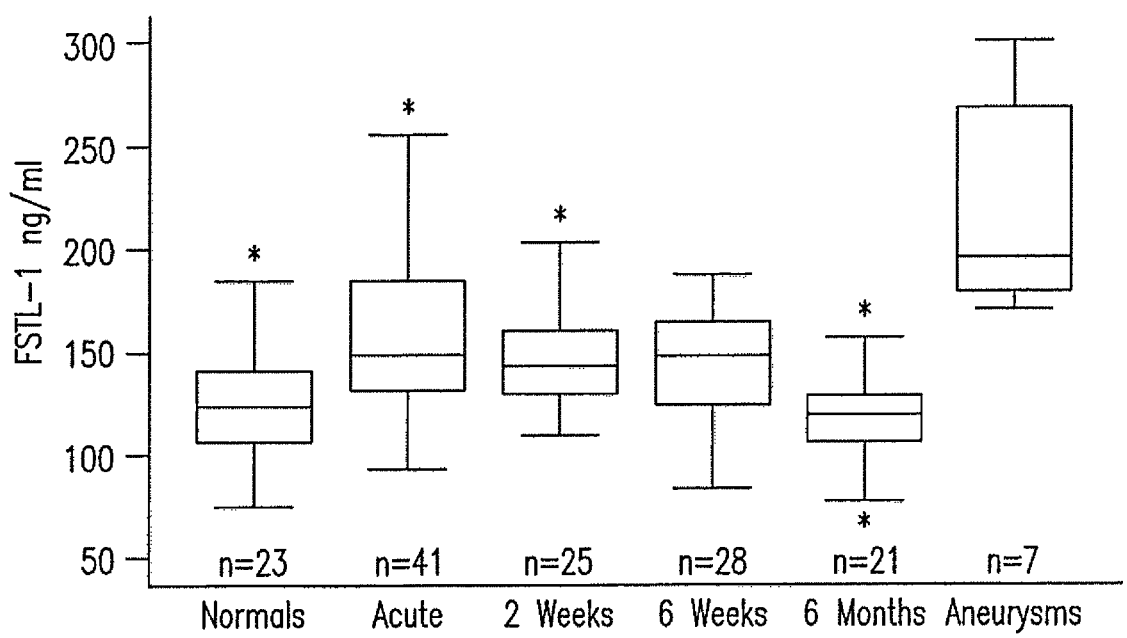

FIG. 9. Median, 25th and 75th percentiles values of plasma FSTL-1. n=number of patients.

Figure 10:
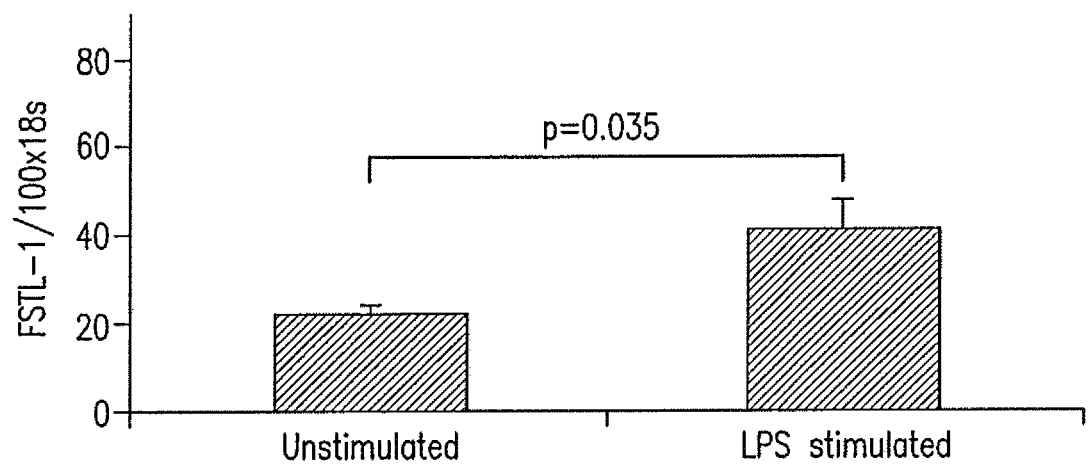

FIG. 10. FSTL-1 mRNA copy number in mouse heart in response to in vivo administration of LPS. Hearts were collected from mice 7 hours following administration of PBS or LPS. mRNA was isolated and subjected to real-time PCR for mouse FSTL-1 transcript. Copy numbers were then normalized to 18 s mRNA. Each bar represents the mean±SEM of 3 mice.

Figure 11:
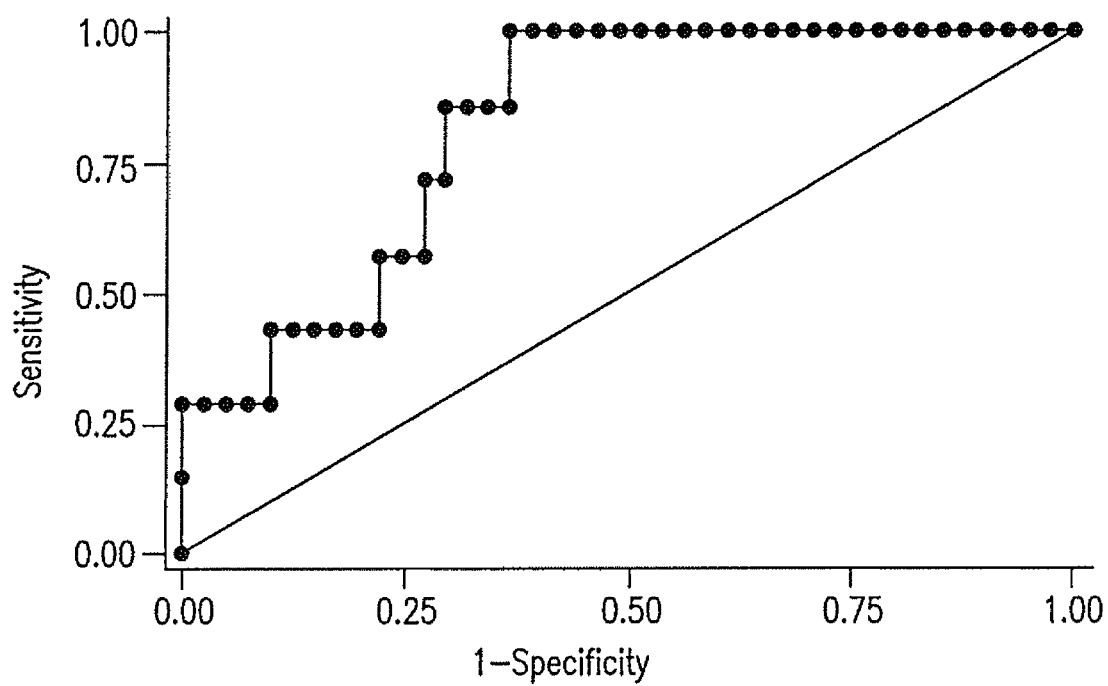

FIG. 11. Receiver Operator Curve analysis shows an area under the curve of 0.8223, (95% CI 0.6863, 0.9583).

5. DETAILED DESCRIPTION OF THE INVENTION

For clarity of description, and not by way of limitation, the detailed description of the invention is divided into the following subsections:

(i) inflammatory disorders;
(ii) methods of measuring FSTL-1;
(iii) methods of diagnosis and
(iv) kits.

5.1 Inflammatory Disorders

The present invention provides for the diagnosis of inflammatory disorders. In non-limiting embodiments, the present invention provides for the diagnosis of inflammatory disorders associated with elevated levels of IL-1β (meaning disorders having a laboratory finding in which serum levels of IL-1β are increased relative to control values and/or which may be treated by inhibiting IL-1β); in specific non-limiting embodiments the increase is by at least 20 percent or at least 30 percent or at least 50 percent over control values during at least a portion of the clinical course of the disorder). Examples of IL-1β-associated disorders that may be diagnosed according to the invention include but are not limited to juvenile idiopathic arthritis; systemic onset juvenile idiopathic arthritis; Kawasaki Disease; rheumatoid arthritis; periodic fever, aphthous stomatitis, pharyngitis, adenitis syndrome ("PFAPA"); urate crystal arthritis (gout); type 2 diabetes; smoldering multiple myeloma; postmyocardial infarction heart failure; and osteoarthritis. Further IL-1β-associated disorders that are categorized as autoinflammatory disorders or probable autoinflammatory disorders, and which may be diagnosed according to the invention, include but are not limited to familial Mediterranean fever ("FMF"); pyogenic arthritis, pyoderma gangrenosum, acne ("PAPA"); cryopyrin-associated periodic syndromes ("CAPS"); hyper-IgD syndrome ("HIDS"); adult and juvenile Still disease; Schnitzler syndrome; TNF receptor associated periodic syndrome ("TRAPS"); Blau syndrome; Sweet syndrome; deficiency in IL-1 receptor antagonist ("DIRA"); recurrent idiopathic pericarditis; macrophage activation syndrome; urticarial vasculitis; antisynthetase syndrome; relapsing chondritis; Behcet disease; Erdheim-Chester syndrome (histiocytosis); synovitis, acne, pustulosis, hyperostosis, osteitis ("SAPHO"), Muckle-Wells and neonatal-onset multisystem inflammatory disease (NOMID), and other disorders described in Dinarello, April 2011, Blood 117(141:3720-3732.

5.2 Methods of Measuring FSTL-1

FSTL-1 may be measured by any method known in the art, including methods of measuring protein levels such as, but not limited to, enzyme-linked immunosorbent assay ("ELISA"); radioimmunoassay; polyacrylamide gel electrophoresis; or Western blot, etc. In certain non-limiting embodiments, levels of mRNA encoding FSTL-1 may be directly or indirectly measured and considered to reflect serum or synovial fluid levels of that protein; for example, mRNA may be prepared from a subject (e.g. patient or control) sample and then the amount of FSTL-1 encoding mRNA in the sample may be determined.

A sample may be collected from or sequestered from a patient. A sample may be, for example, but not by way of limitiation, a serum sample, a blood sample, a plasma sample, a synovial fluid sample, a cerebrospinal fluid sample, a peritoneal fluid sample, or a urine sample.

A subject may be a human or non-human subject, including but not limited to mammalian subjects.

In various non-limiting embodiments, FSTL-1 is measured by a method that comprises reacting FSTL-1 in a subject (e.g. patient or control) sample with a capture ligand to bind FSTL-1 to the capture ligand, and then directly or indirectly detecting the presence of FSTL-1 bound to the capture ligand.

In one set of non-limiting embodiments, FSTL-1 may be measured by the following method. For detection of human FSTL-1 in plasma, Nunc Immunomodule MaxiSorp F8 Framed ELISA plates may be coated with 5 ug/ml polyclonal anti-FSTL1 (AF1694; R&D Systems, Minneapolis, Minn.) in phosphate buffered saline (PBS) and incubated at 4° C. overnight. Plates may then be washed with PBS/0.05% Tween 20 and blocked for one hour with bovine serum albumin (BSA) buffer (1% BSA and 5% sucrose in PBS). Plates may then be washed again, and human plasma samples diluted 1:10 may be added. After washing, 2.5 ug/ml biotinylated monoclonal anti-FSTL1 (MAB1694; R&D systems) may be added for 1 hour. Plates may then be washed again and incubated with Streptavidin-HRP conjugate at 0.25 ug/ml for 20 minutes. BD OptEIA TMB Substrate Reagent may then be added, and plates may be incubated for an additional hour, following which development may be stopped with addition of 1M $H_2SO_4$. Plate absorbance may be read on a microplate reader with dual measurement of 450 nm and 570 nm reference level. A titration of purified FSTL-1 may be used to generate a standard curve from which plasma concentration of samples may be calculated.

In alternative specific, non-limiting examples of the invention, FSTL-1 levels may be measured by the following method. For detection of human FSTL-1 in sera and synovial fluids, standard bind plates (Meso Scale Discovery (MSD), Gaithersburg, Md.) may be coated with 0.2 µg per well goat anti-human FSTL1 (AF1694; R&D Systems, Minneapolis, Minn.) in 0.03% Triton-X100 overnight at 4° C. Plates may be washed with PBS/0.05% Tween-20 and blocked with MSD Human Serum Cytokine Assay Diluent for 1 hour. Human sera and synovial fluids, diluted 1:2 in MSD Human Serum Cytokine Assay Diluent, may be added overnight at 4° C. Plates may be washed and 0.5 µg/ml custom sulfo-tagged polyclonal rabbit anti-FSTL-1 may be added for 4 hours. Plates may be washed, 150 µl/well of 2×MSD Read Buffer may be added, and plates then may be imaged in a MSD SECTOR Imager 2400.

5.3 Methods of Diagnosis

The present invention relates to methods and compositions for diagnosis of inflammatory disorders, and, in non-limiting embodiments, of inflammatory disorders associated with elevated IL-1β, based on increased levels of FSTL-1.

In certain non-limiting embodiments, the present invention provides for a method of diagnosing an inflammatory disorder, or an inflammatory disorder associated with elevated IL-1β, or an autoinflammatory disorder, in a patient, comprising measuring the level of FSTL-1 in a sample of the patient and comparing that level to the level of FSTL-1 measured in a sample of a (healthy) control subject or an average level of FSTL-1 measured in samples from a plurality of control subjects, where a level in the patient that is about 20-60 percent higher, or 30-60 percent higher, or 35-55 percent higher, or 30-50 percent higher, than the level or average level in the control subject or subjects is consistent with a diagnosis of an inflammatory disorder, or an inflammatory disorder associated with elevated IL-1β, or an autoinflammatory disorder, in the patient. In non-limiting examples, the sample may be a serum sample or a synovial fluid sample.

In certain non-limiting embodiments, the present invention provides for a method of diagnosing an inflammatory disorder, or an inflammatory disorder associated with elevated IL-1β, or an autoinflammatory disorder, in a human patient, comprising measuring the level of human FSTL-1 in a sample of the patient and comparing that level to the level of human FSTL-1 measured in a sample of a (healthy human) control subject or an average level of FSTL-1 measured in samples from a plurality of control subjects, where a level in the patient that is about 20-60 percent higher, or 30-60 percent higher, or 35-55 percent higher, or 30-50 percent higher, than the level or average level in the control subject or subjects is consistent with a diagnosis of an inflammatory disorder, or an inflammatory disorder associated with elevated IL-1β, or an autoinflammatory disorder, in the patient. In non-limiting examples, the sample may be a serum sample or a synovial fluid sample.

In non-limiting embodiments, the present invention provides for a method of diagnosing an inflammatory disorder in a human patient comprising measuring the level of human FSTL-1 in a serum sample of the patient, where a level in the patient that is measured to be between about 200 and 300 ng/ml is consistent with a diagnosis of an inflammatory disorder in the patient. The inflammatory disorder, for example, may be an inflammatory disorder associated with elevated levels of interleukin-1β or an autoinflammatory disorder as set forth above, for example, but not limited to, systemic onset juvenile idiopathic arthritis or Kawasaki disease. Said method may, for example, comprise comparing the serum level of human FSTL-1 measured in the patient to the level of human FSTL-1 measured in a serum sample of a healthy human control subject or an average level of human FSTL-1 measured in serum samples from a plurality of healthy human control subjects, where said level in a control subject, or said average level in control subjects, is measured to be between about 125-160 ng/ml.

In certain non-limiting embodiments, the present invention provides for a method of diagnosing SOJIA in a human patient comprising measuring the level of human FSTL-1 in a serum or synovial fluid sample of the patient and comparing that level to the level of human FSTL-1 measured in a serum or synovial fluid sample of a (healthy human) control subject or an average level of human FSTL-1 in serum or synovial fluid samples from a plurality of control subjects, where a level in the patient that is about 20-80 percent higher, or 20-60 percent higher, or 30-60 percent higher, or 35-55 percent higher, or 30-50 percent higher, or 30-80 percent higher, than the level or average level in a control subject or subjects is consistent with a diagnosis of SOJIA for the patient. In a specific, non-limiting embodiment, where the control level in serum is measured to be about 15 ng/ml for a control subject or control subjects, a patient serum level measured to be between about 18 and 25 ng/ml is consistent with a diagnosis of SOJIA. In another specific, non-limiting embodiment, where the control level in synovial fluid is measured to be about 40 ng/ml for a control subject or control subjects, a patient synovial fluid level measured to be between about 60 and 70 ng/ml is consistent with a diagnosis of SOJIA. In yet another specific, non-limiting embodiment, where the control level in serum is measured to be about 125-160 ng/ml for a control subject or control subjects, a patient serum level measured to be between about 200 and 300 ng/ml, or between about 200 and 250 ng/ml, is consistent with a diagnosis of SOJIA. A diagnosis of SOJIA may be further corroborated by determining whether markers of inflammation, including, but not limited to, erythrocyte sedimentation rate ("ESR"), platelet count, and/or C reactive protein, are elevated, where an elevation in at least one of these markers more strongly indicates a diagnosis of SOJIA of active SOJIA in particular. In specific non-limiting examples of the invention, ESR≥20 mm/hr or a platelet count≥380×10$^9$/L would be corroborative of a diagnosis of SOJIA and of active SOJIA in particular.

In particular non-limiting embodiments, the invention further provides for methods of identifying a patient with SOJIA who is at increased risk for developing macrophage activation syndrome ("MAS") comprising detecting, in said patient, a level of FSTL-1 that is increased by 40 percent or more relative to control level(s). In particular non-limiting embodiments, the present invention provides for a method of identifying a patient with SOJIA who is at increased risk for developing or having MAS comprising measuring the level of human FSTL-1 in a serum or synovial fluid sample of the patient and comparing that level to the level of human FSTL-1 in a serum or synovial fluid sample of a (healthy human) control subject or an average level of human FSTL-1 in serum or synovial fluid samples from a plurality of control subjects, where a level in the patient that is 40 percent or greater, 50 percent or greater, and/or 75 percent or greater than the level or average level in a control subject or subjects is consistent with an increased risk that the patient will develop or has MAS. In a specific, non-limiting embodiment, where the control level in serum is measured to be about 125-160 ng/ml for a control subject or control subjects, a patient serum level measured to be between about 220 and 300 ng/ml, or greater than or equal to 230 ng/ml, or greater than or equal to 250 ng/ml, indicates that the subject is at increased risk of developing or having MAS. The increased risk of developing or having MAS may be further corroborated by detecting an elevation in one or more of the following MAS-associated biomarkers: IL-1 receptor, lipocalin 2, MMP8, MMP9, IL-18, and/or genes associated with TLR4/IL1 receptor signaling. Where a patient is deemed to be at increased risk for developing or having MAS, the diagnostic method of the invention may further comprise one or more of: performing a cytologic evaluation of the blood smear; determining the platelet count (where a decreased platelet count (e.g. less than 262×10$^9$/L) supports a diagnosis of MAS); determining the white blood cell count, where a decreased white blood cell count (e.g., less than 4×10$^9$) supports a diagnosis of MAS; and/or determining the level of serum fibrinogen, where a level less than 2.5 g/L is supports a diagnosis of MAS.

In certain non-limiting embodiments, the present invention provides for a method of diagnosing Kawasaki Disease in a human patient comprising measuring the level of human FSTL-1 in a serum sample of the patient and comparing that level to the level of human FSTL-1 measured in a serum sample of a (healthy human) control subject or an average level of human FSTL-1 measured in serum samples from a plurality of control subjects, where a level in the patient that is about 20-80 percent higher, or 20-60 percent higher, or 30-60 percent higher, or 35-55 percent higher, or 30-50 percent higher, or 30-80 percent higher, than the level or average level in a control subject or subjects is consistent with a diagnosis of Kawasaki Disease for the patient. In a specific, non-limiting embodiment, where the control level in serum is measured to be about 120-140 ng/ml for a control subject or control subjects, a patient serum level measured to be between about 165-250 ng/ml is consistent with a diagnosis of Kawasaki Disease.

In additional non-limiting embodiments, the invention provides for methods of identifying a patient with Kawasaki disease who is at increased risk of developing an aortic aneurysm comprising detecting, in said patient, a level of FSTL-1 that is increased by 50 percent or more or by 60 percent or more relative to control level(s). In particular non-limiting embodiments, the present invention provides for a method of identifying a patient with Kawasaki Disease who is at increased risk for developing or having an aortic aneurysm comprising measuring the level of human FSTL-1 in a serum sample of the patient and comparing that level to the level of human FSTL-1 in a serum sample of a (healthy human) control subject or an average level of human FSTL-1 in serum samples from a plurality of control subjects, where a level in the patient that is 60 percent or greater and/or 75 percent or greater than the level or average level in a control subject or subjects is consistent with an increased risk that the patient will develop or has an aortic aneurysm. In a specific, non-limiting embodiment, where the control level in serum is measured to be about 125-160 ng/ml for a control subject or control subjects, a patient serum level measured to be between about 200 and 250 ng/ml, or greater than or equal to 200 ng/ml, indicates that the patient is at increased risk of developing or having an aortic aneurysm. Where a patient is deemed to be at increased risk of developing or having an aortic aneurysm, a further procedure may be recommended, for example but not limited to an angiogram, radiologic, CT or MRI to visualize the aorta.

5.4 Kits

In certain embodiments, the present invention provides for kits that may be used to practice the diagnostic methods of the invention. Said kits may comprise a sample of monoclonal or polyclonal antibody specific for human FSTL-1, where said antibody is optionally detectably labeled (for example, with an enzyme, fluorescent, or radioactive label), together with one or more, two or more, or three or more, or four or more, of the following: an antibody that specifically binds to the anti-human FSTL-1 antibody, an antibody that binds to human C-reactive protein; an antibody that binds to IL-1 receptor, an antibody that binds to lipocalin 2, an antibody that binds to MMP8, an antibody that binds to MMP9, an antibody that binds to IL-18, one or more antibody that binds to the product(s) of genes associated with TLR4/IL1 receptor signaling, and human FSTL-1, which, for example, may be used to create a standard curve of FSTL-1 dilutions.

6. EXAMPLE

FSTL-1 is a Mesenchyme-Derived Inflammatory Protein and May Represent a Biomarker for Systemic Onset Juvenile Rheumatoid Arthritis

6.1 Materials and Methods

Patient Samples

Banked sera and synovial fluids were obtained from patients with JRA defined according to criteria established by the ACR (1; reference list at end of this section 6). Patient demographics are summarized in Table 1, below. The study patients were recruited from the rheumatology clinic at Children's Hospital of Pittsburgh. Banked synovial fluids were also obtained from the Cincinnati Children's Hospital Medical Center JRA Tissue Repository. Control synovial fluids were collected from children with no history of JRA or inflammatory disease who underwent an orthopedic procedure, such as ACL repair. The synovial fluid samples were placed on ice immediately after collection, centrifuged at 400×g for 10 minutes to remove cells and debris and stored at −80° C. The sera were allowed to clot, centrifuged at 3,000×g for 10 minutes to remove red blood cells, and stored at −80° C. The study was approved by the Institutional Review Board at the University of Pittsburgh. Informed consent was obtained from all guardians of patients and assent was obtained from the subjects when appropriate.

TABLE 1

Demographic and clinical characteristics of the study population*

| Characteristic | Oligo (n = 54) | Poly (n = 26) | Systemic (n = 15) | Control (n = 15) |
|---|---|---|---|---|
| Age, years | 9 ± 5.17 | 12 ± 6.17 | 13 ± 6.81 | 12 ± 8.31 |
| Sex, no. (%) | | | | |
| Male | 18 (33) | 9 (35) | 8 (53) | 6 (40) |
| Female | 36 (67) | 17 (65) | 7 (47) | 9 (60) |
| Disease Duration, years | 3 ± 4.35 | 7 ± 5.99 | 7 ± 8.42 | N/A |

*Except where indicated otherwise, values are the mean ± SD.
Oligo = oligoarticular JIA; Poly = polyarticular JIA; Systemic = systemic JIA Mice.

Male DBA/1 mice, 6-10 weeks of age, were purchased from Harlan (Indianapolis, Ind.). Mice were housed in the animal resource facility at the Children's Hospital of Pittsburgh Rangos Research Center (Pittsburgh, Pa.). The study was approved by the Children's Hospital of Pittsburgh's Animal Research and Care Committee. CIA was induced by intra-dermal immunization of DBA/1 mice with bovine collagen type II (Elastin Products, Owensville, Mo.), as previously described (16).

FSTL-1 Immunoassay.

For detection of human FSTL-1 in sera and synovial fluids, standard bind plates (Meso Scale Discovery (MSD), Gaithersburg, Md.) were coated with 0.2 µg per well goat anti-human FSTL1 (AF1694; R&D Systems, Minneapolis, Minn.) in 0.03% Triton-X100 overnight at 4° C. Plates were washed with PBS/0.05% Tween-20 and blocked with MSD Human Serum Cytokine Assay Diluent for 1 hour. Human sera and synovial fluids, diluted 1:2 in MSD Human Serum Cytokine Assay Diluent, were added overnight at 4° C. Plates were washed and 0.5 µg/ml custom sulfo-tagged polyclonal rabbit anti-FSTL-1 was added for 4 hours. Plates were washed, 150 µl/well of 2×MSD Read Buffer was added, and plates were imaged in a MSD SECTOR Imager 2400.

Immunohistochemistry.

Knee joints from mice with CIA were frozen in liquid nitrogen-cooled isopentane. Seven micron sections were prepared with the Cryojane Tape Transfer System (Instrumedics, St. Louis, Mo.). Slides were fixed with 2% paraformaldehyde for 20 minutes and washed with PBS followed by BSA buffer (0.5% BSA and 0.15% glycine in PBS). Slides were blocked with a 1/20 dilution of normal donkey serum (Sigma-Aldrich, St. Louis, Mo.) in BSA buffer and washed three times with BSA buffer. Slides were incubated for 1 hour with 10 µg/ml affinity-purified polyclonal goat anti-mouse FSTL-1 (AF1738; R&D Systems, Minneapolis, Minn.). The slides were washed three times with BSA buffer, and bound antibody was visualized using 4 µg/ml Alexa Fluor 488-conjugated donkey anti-goat IgG (Invitrogen, Carlsbad, Calif.). For identification of fibroblasts, slides were reacted with 1.5 µg/ml rat anti-mouse CD90 (BD Pharmingen, Franklin Lakes, N.J.) and bound antibody was visualized with 2 µg/ml Alexa Fluor 594-conjugated donkey anti-rat IgG. Nuclei were stained with Hoechst 3343 blue (Invitrogen). A coverslip containing a drop of gelvatol was added, and slides were stored at 4° C. until observation. Slides were imaged using an Olympus Fluoroview 1000 (Olympus) confocal microscope or a Nikon TE2000 inverted phase-fluorescence microscope using a 12-bit 1600×1200 element CCD array to capture images (Spot, Diagnostic Instruments, Sterling Heights, Mich.); color, where shown, is assigned to the channel indicated and reflects approximate output fluorescence unless indicated. Filters for green fluorescence were: excitation 450-

490 nm, 510 nm dichroic mirror, 500-570 nm barrier; for red fluorescence: excitation 536-556 nm, 580 nm dichroic mirror, 580-650 nm barrier. Photographs used a NA 0.70 long working distance 40× phase contrast objective.

In Vitro Induction and Detection of FSTL-1.

MC3T3, 3T3-L1, and human fibroblast like synoviocytes derived from patients with rheumatoid arthritis undergoing joint replacement were cultured at a concentration of $3 \times 10^4$ cells/well in 96-well flat bottom plates for 3 days in triplicate with or without the addition of TGF-β (2 ng/ml), IL-113 (10 ng/ml) TNF-α (10 ng/ml), or IL-6 (50 ng/ml). Cell culture supernatants were assayed for mouse or human FSTL-1 by coating Nunc Immunomodule MaxiSorp ELISA plates (Nalgene, Rochester N.Y.) with 5 µg/ml rat anti-mouse FSTL-1 (MAB1738; R&D Systems, Minneapolis, Minn.) or goat anti-human FSTL-1 (AF1694; R&D Systems) overnight at 4° C. Plates were washed with PBS/0.05% Tween-20 and blocked with 1% BSA/5% sucrose/0.05% Tween-20 for 1 hour. Cell culture supernatants were added at appropriate dilutions and held at room temperature for 1 hour. After washing, 5 µg/ml biotin-labeled goat anti-mouse FSTL-1 (AF1738; R&D Systems) or rat-anti-human FSTL-1 (MAB 1694; R&D Systems) was added for 1 hour. Plates were washed and incubated with streptavidin-HRP (Invitrogen, Carlsbad, Calif.), developed with Peroxidase Substrate System ABTS (Kirkegaard & Perry, Gaithersburg, Md.), and absorbance was read at 405 nm on a microplate reader.

6.2 Results

FSTL-1 is Produced in the Joint Space by Cells of the Mesenchymal Lineage.

Fluorescent antibody labeling in frozen sections of joints from mice with CIA was used to determine whether FSTL-1 is produced in joint tissues. FSTL-1 protein was found in cells of the mesenchymal lineage, including osteocytes and chondrocytes (FIG. 1A), adipocytes (FIG. 1B) and fibroblasts (FIG. 1C). No FSTL-1 expression was observed in cells of the hematopoietic lineage, such as macrophages, T cells, and B cells.

FSTL-1 Secretion is Induced in Mesenchymal Lineage Cells by Arthritis-Promoting Cytokines.

Figure 2A:
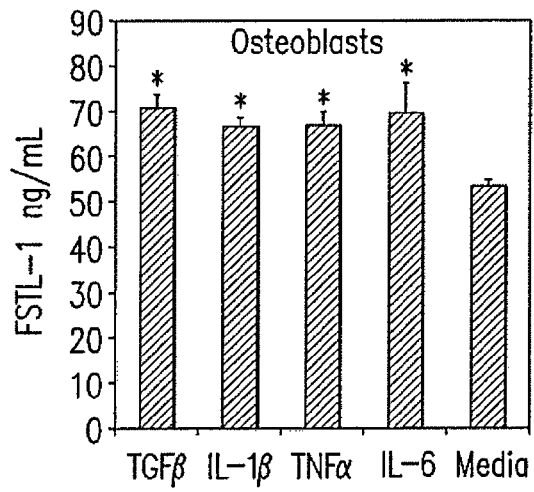
Figure 2B:
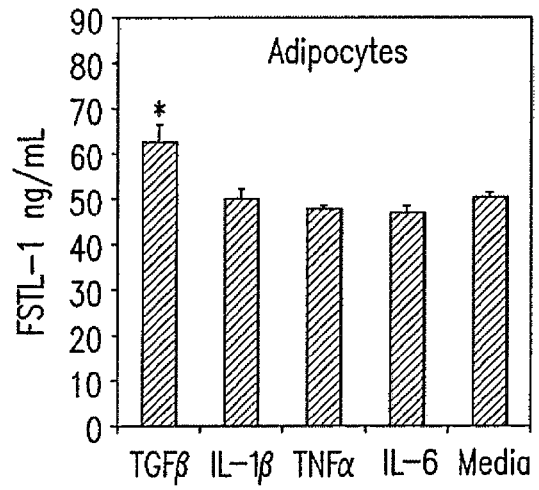
Figure 2C:
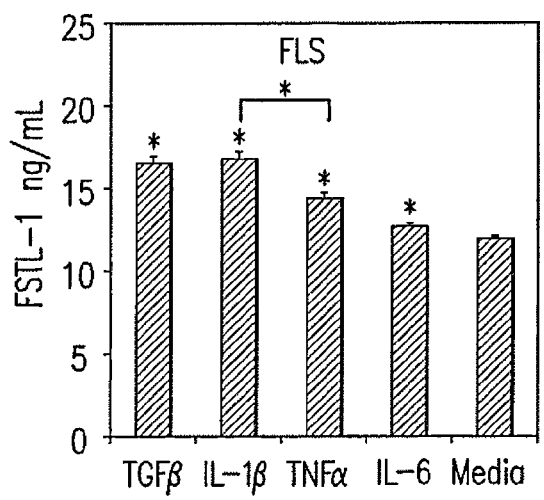
Figure 2D:
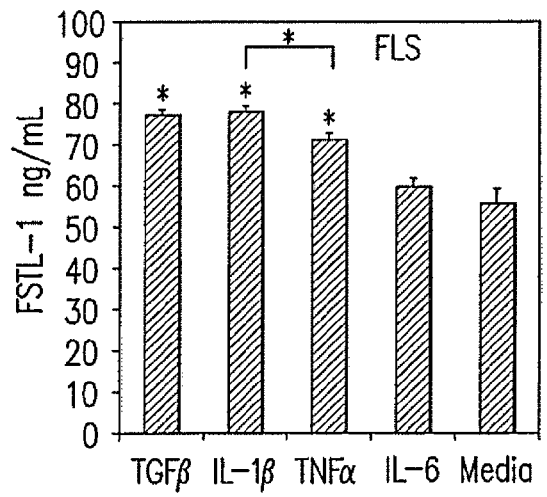

The ability of various inflammatory cytokines to induce FSTL-1 secretion from mesenchymal cells was analyzed. For these experiments, the mouse osteoblast cell line, MC3T3, the mouse adipocyte cell line, 3T3L1, and two human fibroblast-like synoviocyte cell lines derived from hip joints of two patients with RA were utilized. Cells were stimulated with IL-1β, TNF-α, or IL-6. TGF-β was used as a positive control, since FSTL-1 was originally described as a TGF-β inducible gene in MC3T3 cells (9). IL-1β, TNF-α, and IL-6 all stimulated FSTL-1 secretion from osteoblasts (FIG. 2A), while the adipocytes responded only to TGF-β (FIG. 2B). One of the 2 fibroblast-like synoviocyte lines responded to IL-1β, TNF-α, and IL-6 (FIG. 2C) while the other line responded to IL-1β, and TNF-α, but not IL-6 (FIG. 2D). In both fibroblast-like synoviocyte cell lines, IL-1β induced a significantly greater secretion of FSTL-1 than did TNF-α. Monocytic cells (U937), T cells (Jurkat) and B cells (A20) failed to make any detectable FSTL-1, demonstrating that FSTL-1 is not produced by cells of the hematopoietic lineage. FSTL-1 was also not produced by hepatocytes.

FSTL-1 is Elevated in Sera and Synovial Fluids of Patients with Systemic-Onset JRA.

It has previously been shown that FSTL-1 is overexpressed in synovial tissues of mice with arthritis (10). To explore the possibility that FSTL-1 might play a role in JRA, FSTL-1 titers were measured in banked sera (n=55) and synovial fluids (n=74) from children with JRA. Patient demographics are summarized in Table 1.

FSTL-1 Concentrations in Sera.

In sera, the mean FSTL-1 concentration of control subjects was 15.2 ng/ml and all controls had concentrations below 18 ng/ml (FIG. 3). Mean FSTL-1 concentration of the oligoarthritis and polyarthritis JRA subtypes (both 15 ng/ml) did not differ significantly from that of controls. In marked contrast, the mean concentration of the systemic-onset JRA subtype (18 ng/ml) was significantly elevated (p=0.0007). Furthermore, in systemic-onset JRA, a striking correlation was observed between elevated FSTL-1 concentration and laboratory markers of inflammation, defined here as either an ESR≥20 mm/hr or a platelet count ≥$380 \times 10^9$/L (based on the upper limit of normal as reported by the laboratory). Four of the 7 sera from systemic-onset JRA subjects had concentrations above 18 ng/ml, with one as high as 23 ng/ml. All of these 4 subjects with elevated FSTL-1 concentrations had active disease, as defined above, while 2 of the 3 subjects with normal FSTL-1 concentrations had inactive disease. Thus, in all but 1 of the 7 samples from subjects with systemic-onset JRA, elevation of serum FSTL-1 correlated with laboratory evidence of active disease. In contrast, no correlation was observed between FSTL-1 concentrations and active disease in the oligoarthritis and polyarthritis subsets. These data suggest that elevation of serum FSTL-1 is a biomarker for systemic-onset JRA.

FSTL-1 Concentrations in JRA Synovial Fluids.

Only synovial fluids from systemic-onset JRA patients were significantly higher than controls (FIG. 4), again suggesting that elevated FSTL-1 is a marker of the systemic-onset subtype of JRA. Synovial fluid FSTL-1 concentrations were 2-3 fold higher than those observed in serum, indicating that the joint is a source of FSTL-1.

6.3 Discussion

The data presented here support the conclusion that FSTL-1 is a major mediator of the inflammatory cascade that underlies arthritis. For instance, we have demonstrated that over-expression of FSTL-1 in mouse paws by gene transfer resulted in severe paw swelling and arthritis (15), while neutralization of FSTL-1 suppressed arthritis (11). Also, transfection of FSTL-1 into macrophages and fibroblasts lead to up-regulation of proinflammatory cytokines with central roles in chronic arthritis, including IL-1-β and TNF-α (11).

While expression of FSTL-1 in osteoblasts and fibroblasts has been previously reported, the finding that FSTL-1 can be produced by other mesenchymal cells, including adipoctyes and chondrocytes, is novel. These results, along with the observation that synovial fluid levels are 2-3 fold higher than serum levels, support the conclusion that the joint is a primary source of FSTL-1. Furthermore, it supports the concept that the joint matrix, including bone, cartilage, and adipose tissue, is not merely a passive target of destruction by blood-derived immune cells in arthritis; rather, this joint matrix plays an active role in perpetuating and amplifying the inflammatory response by releasing pro-inflammatory mediators, such as FSTL-1.

The present study suggests that systemic-onset JRA is characterized by elevated concentrations of serum and synovial fluid FSTL-1 that are not observed in other forms of JRA. Elevation of serum FSTL-1 correlated closely with markers of disease activity in systemic-onset JRA, including elevated ESR and platelet count, but this correlation was not observed in oligoarthritis or polyarthritis. These data suggest that FSTL-1 may be useful as a biomarker of disease activity in this JRA subtype. An important caveat is that, although the results are statistically-significant, the number of systemic onset samples available to us was small so that these findings should be validated in a larger cohort of patients. Also, because banked samples were used, the clinical data available, other than ESR and platelet counts, was limited.

The specificity for systemic JRA is interesting in light of the finding that FSTL-1 secretion from human fibroblast-like synoviocytes was significantly greater following incubation with IL-1β than with TNF-α. Systemic-onset JRA has recently been shown to have a strong IL-1β gene expression signature (17). Many patients with systemic-onset JRA respond well to the IL-1 receptor antagonist, Anakinra, (17, 18) but less well to anti-TNF therapy (4, 5). However, it is as yet unclear why patients with polyarticular and oligoarticular arthritis did not have elevated FSTL-1 titers, since TNF-α also induced FSTL-1 secretion from fibroblast-like synoviocytes, albeit to a lesser degree, and TNF-α is a central cytokine in polyarticular disease (2, 3). It is possible that the preferential induction of FSTL-1 by IL-1β is more pronounced in vivo than in vitro.

These findings suggest that FSTL-1 may be a useful biomarker in other disorders driven by IL-1β, such as the autoinflammatory syndromes, including Muckle-Wells and neonatal-onset multisystem inflammatory disease (NOMID) (19-22). None of the samples evaluated in the experiments described in this section were from subjects with macrophage activation syndrome (MAS), which is a serious complication of systemic-onset JRA that can lead to rapid deterioration and death if not treated aggressively.

6.4 References

1. Cassidy J T, Levinson J E, Bass J C, Baum J, Brewer E J, Jr., Fink C W, et al. A study of classification criteria for a diagnosis of juvenile rheumatoid arthritis. Arthritis Rheum 1986; 29(2):274-81.
2. Lovell D J, Giannini E H, Reiff A, Cawkwell G D, Silverman E D, Nocton J J, et al. Etanercept in children with polyarticular juvenile rheumatoid arthritis. Pediatric Rheumatology Collaborative Study Group. N Engl J Med 2000; 342(11):763-9.
3. Lovell D J, Giannini E H, Reiff A, Jones O Y, Schneider R, Olson J C, et al. Long-term efficacy and safety of etanercept in children with polyarticular-course juvenile rheumatoid arthritis: interim results from an ongoing multicenter, open-label, extended-treatment trial. Arthritis Rheum 2003; 48(1):218-26.
4. Horneff G, Schmeling H, Biedermann T, Foeldvari I, Ganser G, Girschick H J, et al. The German etanercept registry for treatment of juvenile idiopathic arthritis. Ann Rheum Dis 2004; 63(12):1638-44.
5. Quartier P, Taupin P, Bourdeaut F, Lemelle I, Pillet P, Bost M, et al. Efficacy of etanercept for the treatment of juvenile idiopathic arthritis according to the onset type. Arthritis Rheum 2003; 48(4):1093-101.
6. Rose H M, Ragan C, et al. Differential agglutination of normal and sensitized sheep erythrocytes by sera of patients with rheumatoid arthritis. Proc Soc Exp Biol Med 1948; 68(1):1-6.
7. Sebbag M, Simon M, Vincent C, Masson-Bessiere C, Girbal E, Durieux J J, et al. The antiperinuclear factor and the so-called antikeratin antibodies are the same rheumatoid arthritis-specific autoantibodies. J Clin Invest 1995; 95(6): 2672-9.
8. Young B J, Mallya R K, Leslie R D, Clark C J, Hamblin T J. Anti-keratin antibodies in rheumatoid arthritis. Br Med J 1979; 2(6182):97-9.
9. Shibanuma M, Mashimo J, Mita A, Kuroki T, Nose K. Cloning from a mouse osteoblastic cell line of a set of transforming-growth-factor-beta 1-regulated genes, one of which seems to encode a follistatin-related polypeptide. Eur J Biochem 1993; 217(1):13-9.
10. Thornton S, Sowders D, Aronow B, Witte D P, Brunner H I, Giannini E H, et al. DNA microarray analysis reveals novel gene expression profiles in collagen-induced arthritis. Clin Immunol 2002; 105(2):155-68.
11. Clutter S D, Wilson D C, Marinov A D, Hirsch R. Follistatin-like protein 1 promotes arthritis by up-regulating IFN-gamma. J Immunol 2009; 182(1):234-9.
12. Tanaka M, Ozaki S, Osakada F, Mori K, Okubo M, Nakao K. Cloning of follistatin-related protein as a novel autoantigen in systemic rheumatic diseases. Int Immunol 1998; 10(9):1305-14.
13. Kawabata D, Tanaka M, Fujii T, Umehara H, Fujita Y, Yoshifuji H, et al. Ameliorative effects of follistatin-related protein/TSC-36/FSTL1 on joint inflammation in a mouse model of arthritis. Arthritis Rheum 2004; 50(2):660-8.
14. Tanaka M, Ozaki S, Kawabata D, Kishimura M, Osakada F, Okubo M, et al. Potential preventive effects of follistatin-related protein/TSC-36 on joint destruction and antagonistic modulation of its autoantibodies in rheumatoid arthritis. Int Immunol 2003; 15(1):71-77.
15. Miyamae T, Marinov A D, Sowders D, Wilson D C, Devlin J, Boudreau R, et al. Follistatin-like protein-1 is a novel proinflammatory molecule. J Immunol 2006; 177 (7):4758-62.
16. Hughes C, Wolos J A, Giannini E H, Hirsch R. Induction of T cell anergy in an experimental model of autoimmunity using non-mitogenic anti-CD3 monoclonal antibody. J Immunol 1994; 153:3319-3325.
17. Pascual V, Allantaz F, Arce E, Punaro M, Banchereau J. Role of interleukin-1 (IL-1) in the pathogenesis of systemic onset juvenile idiopathic arthritis and clinical response to IL-1 blockade. J Exp Med 2005; 201(9):1479-86.
18. Irigoyen P I, Olson J, Hom C, Ilowite N T. Treatment of systemic onset juvenile rheumatoid arthritis with anakinra. Arthritis Rheum 2004; 50:S437.
19. Hawkins P N, Bybee A, Aganna E, McDermott M F. Response to anakinra in a de novo case of neonatal-onset multisystem inflammatory disease. Arthritis Rheum 2004; 50(8):2708-9.
20. Hawkins P N, Lachmann H J, McDermott M F. Interleukin-1-receptor antagonist in the Muckle-Wells syndrome. N Engl J Med 2003; 348(25):2583-4.
21. Hoffman H M, Rosengren S, Boyle D L, Cho J Y, Nayar J, Mueller J L, et al. Prevention of cold-associated acute inflammation in familial cold autoinflammatory syndrome by interleukin-1 receptor antagonist. Lancet 2004; 364(9447): 1779-85.
22. Lovell D J, Bowyer S L, Solinger A M. Interleukin-1 blockade by anakinra improves clinical symptoms in patients with neonatal-onset multisystem inflammatory disease. Arthritis Rheum 2005; 52(4):1283-6.

7. EXAMPLE

FSTL-1 Promotes Arthritis by Enhancing Cytokine/Chemokine Gene Expression

The aim of the experiments described in this section was to determine the mechanism by which FSTL-1 promotes arthritis, focusing on FSTL-1 as a putative mediator of pro-inflammatory cytokine and chemokine synthesis.

7.1 Materials and Methods

CIA was induced in mice hypomorphic for FSTL-1 that were generated using a genetrap technique, resulting in a significant reduction of FSTL-1 protein expression.

Arthritis was assessed by measuring paw swelling and using a qualitative arthritic index.

Mesenchymal stromal cells (MSC) were isolated from the bone marrow of wild type and hypomorphic mice.

To suppress FSTL-1 expression, mouse stromal ST2 cells were transduced with a lentivirus encoding mouse FSTL-1 short hairpin RNA. MSC and ST2 cells were stimulated with IL-1β, TNF-α, or IL-6. Monocytic U937 cells, which do not normally express FSTL-1, were transfected with FSTL-1 and stimulated with phorbol myristate acetate (PMA) and lipopolysaccharide (LPS). The levels of FSTL-1, IL-6, IL-8 and monocyte chemotactic protein-1 (MCP-1) were assessed by ELISA.

7.2 Results

In CIA, a significant correlation was found between serum FSTL-1 levels and both paw swelling and the arthritic index (r=0.399, p<0.01; r=0.496, p<0.05, respectively). FSTL-1 up-regulated IL-6, IL-8 and MCP-1 production in PMA- and LPS-stimulated U937 cells. Knockdown of endogenous FSTL-1 expression suppressed IL-6 and MCP-1 production by stimulated stromal ST2 cells and MSC. FSTL-1 protein could be induced in vivo after treatment of mice with LPS.

7.3 Conclusions

These findings demonstrate that FSTL-1 directly up-regulates pro-inflammatory mediators important in the pathogenesis of arthritis and that serum levels of FSTL-1 correlate with severity of arthritis.

8. EXAMPLE

Serum FSTL-1 is Elevated in Systemic Juvenile Idiopathic Arthritis and is a Biomarker for Macrophage Activation Syndrome

8.1 Materials and Methods

FSTL-1 serum levels were measured by ELISA in 27 patients with sJIA, including 6 patients who developed MAS, as well as in 15 normal controls. Levels were correlated with CD163 and sIL2Ra expression. Peripheral blood mononuclear cells (PBMC) were separated on Ficoll gradients, and RNA was analyzed to evaluate differential gene expression.

8.2 Results

FSTL-1 serum levels are elevated at the time of initial diagnosis of sJIA, as compared to controls (mean of 216.3 ng/ml vs. 156.1 ng/ml, p=0.01). FSTL-1 levels decreased during the course of treatment (FIG. 5A; mean of 132.5 ng/ml after 24 months, p=0.001). Especially high levels of FSTL-1 were present in patients during acute MAS (mean of 231.5 ng/ml). In 3 patients for whom paired samples were available pre- and post-treatment for MAS, FSTL-1 levels changed from a mean of 289.5 ng/ml to a mean of 124.0 ng/ml, p=0.08 (FIG. 5B). Patients with elevated FSTL-1 levels showed increased expression of markers previously associated with MAS, including CD163. PBMC from these patients also showed a 2-fold or greater increase in expression levels of IL-1 receptor, Lipocalin 2, MMP-8, MMP-9, IL-18, as well as other genes associated with TLR4/IL1R signaling (p<0.05).

8.3 Discussion

Systemic juvenile idiopathic arthritis (sJIA) can be complicated by macrophage activation syndrome (MAS), an often fatal disorder characterized by multisystem organ failure. IL-1β and IL-6 are key inflammatory mediators in SJIA and blockade of these cytokines can ameliorate disease activity in a subset of patients. As discussed in section 6, above, FSTL-1 can increase secretion of IL-1β and IL-6 from monocytes and mesenchymal stromal cells (MSC). The experiments described in this section were performed to determine how FSTL-1 levels correlate with measures of clinical disease activity and development of MAS. It was demonstrated that serum FSTL-1 is elevated in clinically active sJIA and increased FSTL-1 correlates with the development of MAS. Patients with elevated levels of FSTL-1 had increased expression of Interleukin-1 and TLR4 related genes, and may represent a subgroup with more severe disease.

9. EXAMPLE

FSTL-1 is Elevated in Kawasaki Disease and Associated with Coronary Aneurysm Formation

9.1 Materials and Methods

Patient Samples.

Banked plasma samples were obtained from patients with KD whose diagnosis was made through established clinical criteria (19). Banked samples were obtained through the pediatric cardiology clinics and inpatient services at Cincinnati Children's Hospital Medical Center and from Northwestern University Children's Memorial Hospital. Serial samples from 41 individual patients were obtained at acute presentation (prior to IVIG), and, when available, at 2 weeks, 6 weeks, and 6 months following presentation. An additional 6 patients did not have an acute sample but had samples at later time points. Seven additional samples were obtained from patients with acute KD who subsequently developed CAA. Control plasma samples were obtained from 23 children with no history of inflammatory disease who underwent surgical procedures including hernia repair, tonsillectomy and adenoidectomy, and simple ophthalmologic procedures. Use of samples was approved by the Institutional Review Board at the University of Pittsburgh. Patient demographics are summarized in Table 2, which is at the end of this section.

FSTL-1 ELISA.

For detection of human FSTL-1 in plasma, Nunc Immunomodule MaxiSorp F8 Framed ELISA plates were coated with 5 ug/ml polyclonal anti-FSTL1 (AF1694; R&D Systems, Minneapolis, Minn.) in phosphate buffered saline (PBS) and incubated at 4° C. overnight. Plates were then washed with PBS/0.05% Tween 20 and blocked for one hour with bovine serum albumin (BSA) buffer (1% BSA and 5% sucrose in PBS). Plates were washed again, and human plasma samples diluted 1:10 were added. After washing, 2.5 ug/ml biotinylated monoclonal anti-FSTL1 (MAB1694; R&D systems) was added for 1 hour. Plates were washed again and incubated with Streptavidin-HRP conjugate at 0.25 ug/ml for 20 minutes. BD OptEIA TMB Substrate Reagent was added, and plates were incubated for an additional hour, following which development was stopped with addition of 1M H2SO4. Plate absorbance was read on a microplate reader with dual measurement of 450 nm and 570 nm reference level. A titration of purified FSTL-1 was used to generate a standard curve from which plasma concentration of samples was calculated.

Mice.

Male DBA/11 mice, 6-9 weeks of age, were purchased from Harlan Laboratories (Indianapolis, Ind.). Mice were housed in the animal resource facility at the Children's Hospital of Pittsburgh Rangos Research Center (Pittsburgh, Pa.). Mice were intraperitoneally injected with 200 ul sterile phosphate buffered saline (PBS) containing 50 □g lipopolysaccharide (LPS). Controls were intraperitoneally injected with PBS only. After 7 hours, mice were sacrificed and perfused with 10 ml PBS. The hearts were harvested and ground into a powder using a mortar and pestle while on dry ice. Samples were stored at −80 C freezer.

Quantitative RT-PCR.

Total RNA was isolated from mouse heart tissue using Invitrogen's RNA TRIzol Reagent (Invitrogen, Carlsbad, Calif.) following the manufacturer's instructions. cDNA was synthesized with random hexamer oligonucleotides using 1 ug of RNA and Invitrogen's SuperScript II Reverse Transcriptase Kit. PCR was performed in a Light-Cycler (Mx3000P; Stratagene) using Brilliant SYBR Green QPCR Master Mix (Stratagene) according to the protocol (95° C. hot start for 10 min followed by 40 amplification cycles, denaturation at 95° C., primer annealing at 59° C., and amplicon extension at 72° C.) using oligonucleotide primer sets for mouse FSTL1 (forward 5' AACAGCCATCAACATCACCA-3' (SEQ ID NO:1); reverse 5'-GGCACTTGAGGAACTCT-TGG-3' (SEQ ID NO:2)) The copy number (number of transcripts) of amplified products was calculated from a standard curve obtained by plotting known input concentrations of plasmid DNA and normalized to total RNA content using 18 s RNA as a housekeeping gene.

Statistical Analysis.

Statistical analysis was performed using STATA version 11. Sensitivity and specificity for aneurysm development by FSTL-1 concentration cutpoint was calculated, as well as positive predictive values. A Receiver Operating Curve (ROC) of FSTL-1 levels at non-aneurysm and aneurysm status was constructed. Mean values were compared by use of Student's t test to determine statistical differences between experimental groups. All reported p values are 2-sided and considered significant at p<0.05.

9.2 Results

FSTL-1 is Elevated in the Blood of Patients with Acute KD.

In order to determine whether patients with acute KD had elevation in FSTL-1 levels, plasma samples from 54 patients with KD were assayed. Of these patients, 7 were known to have developed coronary artery aneurysms. Patients had an initial sample collected during acute disease (prior to IVIG). When possible, additional samples were collected at 2 weeks, 6 weeks, and 6 months post presentation. As shown in FIG. 6, the mean and standard error of the mean (SEM) FSTL-1 level in acute KD was 169.7±6.9 ng/ml, compared to 128.3±6.1 ng/ml in controls (p<0.001). Mean FSTL-1 levels declined to 150.3±5.6 ng/ml at 2 weeks (p value not significantly different from acute time point) and 141.8±4.9 ng/ml at 6 weeks (p=0.03 compared to acute time point). FSTL-1 levels declined further to a level of 119.6±5.2 ng/ml at 6 months, which was not statistically different from normal controls, but significantly different from the acute time point (p<0.001). Paired data analysis by paired t-test of all patients with an initial (acute) time point and a recovery (6 month post presentation) time point also showed statistical significance, p=0.012 (FIG. 7).

Patients Developing CAA have Higher FSTL-1 Levels in the Acute Phase than Patients Who do not.

It was then determined whether FSTL-1 level during acute disease might be a useful predictor for the risk of developing CAA. The acute FSTL-1 levels in the 7 patients who went on to develop aneurysms were compared to the FSTL-1 levels in the 47 patients who did not develop aneurysms. As shown in FIG. 8, the mean FSTL-1 level in patients who developed aneurysms was significantly higher than patients who did not (219.2±20.9 ng/ml versus 161.2±7.2 ng/ml; p=0.024). As shown in FIG. 9, patients who developed CAA had substantially higher levels of FSTL-1 at presentation than did patients without CAA at all stages of disease. The median, 25th and 75th percentiles FSTL-1 values at presentation in patients who did not develop CAA was 148.5 ng/ml, 130.4 ng/ml and 183.6 ng/ml. Median, 25th and 75th percentiles FSTL-1 values at presentation in patients who did develop CAA was 195.5 ng/ml, 177.8 ng/ml and 268.7 ng/ml.

Transcription of FSTL-1 Gene is Increased in the Mouse Heart in Response to LPS Stimulation.

FSTL-1 production is known to be induced in the mouse heart by ischemic injury (13). It was queried whether FSTL-1 is induced in the heart and the coronary arteries in response to an acute systemic inflammatory condition such as KD. LPS was administered to mice as a surrogate of an acute systemic inflammatory insult. Mice were sacrificed 7 hours later and the hearts were collected and assayed by QT-PCR for FSTL-1 transcript. FSTL-1 transcript number was significantly increased approximately 2-fold, compared to control mice injected with PBS (FIG. 10).

FSTL-1 Concentration has Strong Sensitivity and Specificity as a Biomarker for Aneurysm Development.

The ROC analysis for FSTL-1 levels at non-aneurysm and aneurysm status had an area under the curve of 0.8223, (95% CI 0.6863, 0.9583), corresponding to good accuracy of FSTL-1 plasma concentration for aneurysm status (FIG. 11). Using the ROC, a threshold of 178 ng/ml yielded a sensitivity of 85%, with specificity of 71% (Table 3. at the end of this section).

9.3 Discussion

As described above, FSTL-1 induces inflammation in mice and is associated with elevated pro-inflammatory cytokines such as IL-1 and IL-6 (12, 16, 18). FSTL-1 was also found to be elevated in the blood and synovial fluids of children with active systemic Juvenile Idiopathic Arthritis (18), an illness with clinical features that resemble KD. The results of the study described in this section suggest that high levels of FSTL-1, which is produced by cardiac myocytes, might be a biomarker for development of CAA in KD.

Development of CAA is the major cause of morbidity and mortality associated with KD. Efforts to define clinical or serological risk factors for the development of CAA have been described over the last 30 years. However, none of these methods are widely used, and some have not been independently validated. These risk factors have included non-coronary cardiac abnormalities (20), incomplete clinical presentation at very young ages, and resistance to IVIG therapy at older ages (21, 22). Clinical scoring mechanisms to predict development of CAA have been developed that utilize neutrophil and band counts, hemoglobin concentrations, platelet counts, and temperature on the day after infusion of IVIg (23). Nakano et al. (24) and Iwasa et al. (25) identify, among other findings, lab markers such as high white blood cell count, thrombocytopenia, anemia, C-reactive protein levels, age of presentation and male sex as risk factors for development of aneurysm formation. Koren et al. (26) noted that children with CAA had significantly higher temperature during days 10 to 13 of the disease.

Lin et al. investigated other serologic markers for development of CAA including IL-6, TNF-α and soluble IL-2 receptor (27). This evaluation included multiple monthly blood samples and showed that elevated levels of IL-6 and IL-8 in the first week of illness could predict development of CAA. The findings reported here indicate that elevated FSTL-1 levels correlate with increased risk of development of CAA in KD, suggesting that a simple blood test at the time of diagnosis might provide high sensitivity and specificity in identifying patients at high risk. Limitations to this study include the relatively small numbers of patients in the CAA group, as well as the overrepresentation of Hispanic patients in this group. Additionally, all of the patients included met the criteria for complete KD, and we cannot generalize the findings to patients with atypical or incomplete KD.

Despite these limitations, the results herein are consistent with reports that FSTL-1 expression has been shown to be increased in the heart in the setting of cardiac injury and may play a protective role against hypoxic injury to myocytes (13). FSTL-1 was also found to be elevated in patients with heart failure, and FSTL-1 staining was seen in myocytes and vascular endothelial cells of capillaries, small vessels, and smooth muscle cells of larger vessels in these patients (15).

Alterations in eNOS expression have been found to be associated with aneurysm formation both in mouse and human models of aneurysmal disease. Aged eNOS knockout mice have decreased aneurysm formation in comparison to wild type mice (28) suggesting that eNOS activity contributes to aneurysm formation. Polymorphisms in the eNOS gene have been shown to predispose individuals to develop abdominal aortic aneurysms (29), and alterations in nitric oxide production has been shown to cause development of cerebral aneurysms in rats (30). Finally, histopathologic analysis of coronary artery aneurysms in KD demonstrates decreased eNOS staining, among other features of coronary artery senescence (31). FSTL-1 overexpression has recently been shown to improve the revascularization of ischemic limbs in wild type mice, enhance endothelial cell differentiation and migration, and lead to phosphorylation and activation of endothelial nitric oxide synthase (eNOS) (14). Furthermore, FSTL-1 overexpression did not lead to revascularization in mice deficient in eNOS. These actions of FSTL-1 on vascular endothelium through the Akt-eNOS signaling pathway thus suggests a mechanism by which elevated expression of FSTL-1 might contribute to aneurysm formation in KD.

9.4 References

1. Kawasaki T. Acute febrile mucocutaneous syndrome with lymphoid involvement with specific desquamation of the fingers and toes in children. *Arerugi.* 1967; 16(3):178-222.
2. Taubert K A, Rowley A H, Shulman S T. Nationwide survey of Kawasaki disease and acute rheumatic fever. *J Pediatr.* 1991; 119(2):279-282.
3. Galeotti C, Bayry J, Kone-Paut I, Kaveri S V. Kawasaki disease: aetiopathogenesis and therapeutic utility of intravenous immunoglobulin. *Autoimmun Rev.* 9(6):441-448.
4. Rowley A H, Shulman S T. New developments in the search for the etiologic agent of Kawasaki disease. *Curr Opin Pediatr.* 2007; 19(1):71-74.
5. Nakamura Y, Yashiro M, Uehara R, Sadakane A, Chihara I, Aoyama Y, et al. Epidemiologic features of Kawasaki disease in Japan: results of the 2007-2008 nationwide survey. *J Epidemiol.* 20(4):302-307.
6. Newburger J W, Takahashi M, Burns J C, Beiser A S, Chung K J, Duffy C E, et al. The treatment of Kawasaki syndrome with intravenous gamma globulin. *N Engl J. Med.* 1986; 315(6):341-347.
7. Burns J C, Glode M P. Kawasaki syndrome. *Lancet.* 2004; 364(9433):533-544.
8. Terai M, Shulman S T. Prevalence of coronary artery abnormalities in Kawasaki disease is highly dependent on gamma globulin dose but independent of salicylate dose. *J Pediatr.* 1997; 131(6):888-893.
9. Kato H, Sugimura T, Akagi T, Sato N, Hashino K, Maeno Y, et al. Long-term consequences of Kawasaki disease. A 10- to 21-year follow-up study of 594 patients. *Circulation.* 1996; 94(6):1379-1385.
10. Gordon J B, Kahn A M, Burns J C. When children with kawasaki disease grow up myocardial and vascular complications in adulthood. *J Am Coll Cardiol.* 2009; 54(21): 1911-1920.
11. Negoro N, Nariyama J, Nakagawa A, Katayama H, Okabe T, Hazui H, et al. Successful catheter interventional therapy for acute coronary syndrome secondary to kawasaki disease in young adults. *Circ J.* 2003; 67(4):362-365.
12. Shibanuma M, Mashimo J, Mita A, Kuroki T, Nose K. Cloning from a mouse osteoblastic cell line of a set of transforming-growth-factor-beta 1-regulated genes, one of which seems to encode a follistatin-related polypeptide. *Eur J Biochem.* 1993; 217(1): 13-19.
13. Oshima Y, Ouchi N, Sato K, Izumiya Y, Pimentel D R, Walsh K. Follistatin-like 1 is an Akt-regulated cardioprotective factor that is secreted by the heart. *Circulation.* 2008; 117(24):3099-3108.
14. Ouchi N, Oshima Y, Ohashi K, Higuchi A, Ikegami C, Izumiya Y, et al. Follistatin-like 1, a secreted muscle protein, promotes endothelial cell function and revascularization in ischemic tissue through a nitric-oxide synthase-dependent mechanism. *J Biol Chem.* 2008; 283(47): 32802-32811.
15. Lara-Pezzi E, Felkin L E, Birks E J, Sarathchandra P, Panse K D, George R, et al. Expression of follistatin-related genes is altered in heart failure. *Endocrinology.* 2008; 149(11):5822-5827.
16. Miyamae T, Marinov A D, Sowders D, Wilson D C, Devlin J, Boudreau R, et al. Follistatin-like protein-1 is a novel proinflammatory molecule. *J Immunol.* 2006; 177 (7):4758-4762.
17. Clutter S D, Wilson D C, Marinov A D, Hirsch R. Follistatin-like protein 1 promotes arthritis by up-regulating IFN-gamma. *J Immunol.* 2009; 182(1):234-239.
18. Wilson D C, Marinov A D, Blair H C, Bushnell D S, Thompson S D, Chaly Y, et al. Follistatin-like protein 1 is a mesenchyme-derived inflammatory protein and may represent a biomarker for systemic-onset juvenile rheumatoid arthritis. *Arthritis Rheum.* 62(8):2510-2516.
19. Diagnostic guidelines for Kawasaki disease. *Circulation.* 2001; 103(2):335-336.
20. Printz B F, Sleeper L A, Newburger J W, Minich L L, Bradley T, Cohen M S, et al. Noncoronary cardiac abnormalities are associated with coronary artery dilation and with laboratory inflammatory markers in acute Kawasaki disease. *J Am Coll Cardiol.* 57(1):86-92.

21. Song D, Yeo Y, Ha K, Jang G, Lee J, Lee K, et al. Risk factors for Kawasaki disease-associated coronary abnormalities differ depending on age. *Eur J Pediatr.* 2009; 168(11):1315-1321.

22. Yeo Y, Kim T, Ha K, Jang G, Lee J, Lee K, et al. Incomplete Kawasaki disease in patients younger than 1 year of age: a possible inherent risk factor. *Eur J Pediatr.* 2009; 168(2): 157-162.

23. Beiser A S, Takahashi M, Baker A L, Sundel R P, Newburger J W. A predictive instrument for coronary artery aneurysms in Kawasaki disease. US Multicenter Kawasaki Disease Study Group. *Am J Cardiol.* 1998; 81(9):1116-1120.

24. Nakano H, Ueda K, Saito A, Tsuchitani Y, Kawamori J, Miyake T, et al. Scoring method for identifying patients with Kawasaki disease at high risk of coronary artery aneurysms. *Am J Cardiol.* 1986; 58(9):739-742.

25. Iwasa M, Sugiyama K, Ando T, Nomura H, Katoh T, Wada Y. Selection of high-risk children for immunoglobulin therapy in Kawasaki disease. *Prog Clin Biol Res.* 1987; 250:543-544.

26. Koren G, Lavi S, Rose V, Rowe R. Kawasaki disease: review of risk factors for coronary aneurysms. *J Pediatr.* 1986; 108(3):388-392.

27. Lin C Y, Lin C C, Hwang B, Chiang B N. Cytokines predict coronary aneurysm formation in Kawasaki disease patients. *Eur J Pediatr.* 1993; 152(4):309-312.

28. Pimiento J M, Maloney S P, Tang P C, Muto A, Westvik T S, Fitzgerald T N, et al. Endothelial nitric oxide synthase stimulates aneurysm growth in aged mice. *J Vasc Res.* 2008; 45(3):251-258.

29. Atli F H, Manduz S, Katrancioglu N, Ozum U, Disli O M, Atahan E, et al. eNOS G894T polymorphism and abdominal aortic aneurysms. *Angiology.* 61(2): 125-130.

30. Tamura T, Jamous M A, Kitazato K T, Yagi K, Tada Y, Uno M, et al. Endothelial damage due to impaired nitric oxide bioavailability triggers cerebral aneurysm formation in female rats. *J Hypertens.* 2009; 27(6): 1284-1292.

31. Fukazawa R, Ikegam E, Watanabe M, Hajikano M, Kamisago M, Katsube Y, et al. Coronary artery aneurysm induced by Kawasaki disease in children show features typical senescence. *Circ J.* 2007; 71(5):709-715.

TABLE 2

| Patient Characteristic | KD without aneurysm (n = 47) | KD with aneurysm (n = 7) | Control (n = 23) |
|---|---|---|---|
| Age, months* | 42.09 | 41.7 | 43.22 |
| Sex† | | | |
| Male | 29 (64%) | 5 | 17 (74%) |
| Female | 17 (36%) | 2 | 6 (26%) |
| Unknown | 1 | | |
| Race‡ | | | |
| White | 25 | 2 | 17 |
| Black | 17 | 1 | 6 |
| Other/unknown | 5 | 4 (1 Asian, 3 Hispanic) | — |

*p value age: KD w/o aneurysm vs. control = 0.87 (t test), KD w/o aneurysm vs. KD with aneurysm = 0.96 (t test)

TABLE 3

| FSTL-1 Cutpoint (ng/ml) | Sensitivity | Specificity | Likelihood Ratio | Positive Predictive Value (5% prevalence) | Positive Predictive Value (25% prevalence) |
|---|---|---|---|---|---|
| 130 | 100% | 24% | 1.3 | 6.5% | 30% |
| 170 | 100% | 63% | 2.7 | 12.6% | 47% |
| 178 | 85% | 71% | 2.9 | 13.4% | 49% |
| 214 | 43% | 85% | 2.9 | 13.4% | 49% |
| 250 | 29% | 92% | 3.9 | 17% | 56% |

Sensitivity, Specificity, Likelihood ratio and Positive Predictive Values (for 5% and 25% prevalence of coronary artery aneurysms in Kawasaki disease)

Various references are cited herein, the contents of which are hereby incorporated by reference in their entireties.

What is claimed is:

1. A method of diagnosing an inflammatory disorder in a human patient comprising:
    (a) measuring the level of human FSTL-1 in a sample collected from the patient suspecting having an inflammatory disorder by an enzyme-linked immunosorbent assay; and
    (b) diagnosing that the patient has an inflammatory disorder if the level of human FSTL-1 in the sample of the patient is measured to be between about 200 and 300 ng/ml, and
    wherein the inflammatory disorder is systemic onset juvenile idiopathic arthritis or Kawasaki disease.

2. The method of claim 1, comprising comparing the level of human FSTL-1 measured in the sample of the patient to the level of human FSTL-1 measured in a sample of a healthy human control subject or an average level of human FSTL-1 measured in samples from a plurality of healthy human control subjects, where said level of human FSTL-1 in the sample of the control subject, or said average level of human FSTL-1 in the samples of the control subjects, is measured to be between about 125-160 ng/ml.

3. The method of claim 1, where the sample is a serum sample.

4. The method of claim 1, where the level of FSTL-1 is measured by a method that comprises reacting FSTL-1 in a subject sample with a capture ligand to bind FSTL-1 to the capture ligand, and then directly or indirectly detecting the presence of FSTL-1 bound to the capture ligand.

5. The method of claim 2, where the level of FSTL-1 is measured by a method that comprises reacting FSTL-1 in a subject sample with a capture ligand to bind FSTL-1 to the capture ligand, and then directly or indirectly detecting the presence of FSTL-1 bound to the capture ligand.

6. A method of identifying a patient with systemic onset juvenile idiopathic arthritis who is at increased risk for developing macrophage activation syndrome comprising:
    (a) measuring the level of human FSTL-1 in a sample collected from the patient by an enzyme-linked immunosorbent assay; and
    (b) identifying the patient with systemic onset juvenile idiopathic arthritis as being at increased risk for developing macrophage activation syndrome if the level of human FSTL-1 in the sample of the patient is measured to be increased by about 40 percent or more relative to control levels.

7. The method of claim 6, where the serum level of human FSTL-1 in the sample of the patient is measured to be about 230 ng/ml or greater.

8. The method of claim 6, where the level of FSTL-1 is measured by a method that comprises reacting FSTL-1 in a subject sample with a capture ligand to bind FSTL-1 to the capture ligand, and then directly or indirectly detecting the presence of FSTL-1 bound to the capture ligand.

9. A method of identifying a patient with Kawasaki disease who is at increased risk for developing macrophage activation syndrome comprising:
   a) measuring the level of human FSTL-1 in a sample collected from the patient by an enzyme-linked immunosorbent assay; and
   (b) identifying the patient with Kawasaki disease as being at increased risk for developing macrophage activation syndrome if the level of human FSTL-1 in the sample of the patient is measured to be increased by about 50 percent or more relative to control levels.

10. The method of claim 9, where the serum level of human FSTL-1 in the sample of the patient is measured to be about 200 ng/ml or greater.

11. The method of claim 9, where the level of FSTL-1 is measured by a method that comprises reacting FSTL-1 in a subject sample with a capture ligand to bind FSTL-1 to the capture ligand, and then directly or indirectly detecting the presence of FSTL-1 bound to the capture ligand.

* * * * *

UNITED STATES PATENT AND TRADEMARK OFFICE
CERTIFICATE OF CORRECTION

| | | |
|---|---|---|
| PATENT NO. | : 8,741,584 B2 | Page 1 of 1 |
| APPLICATION NO. | : 13/758405 | |
| DATED | : June 3, 2014 | |
| INVENTOR(S) | : Raphael Hirsch and David C. Wilson | |

It is certified that error appears in the above-identified patent and that said Letters Patent is hereby corrected as shown below:

ON THE TITLE PAGE:

At item (63):

Delete "Continuation of application No. PCT/US2011/046742, filed May 5, 2011."

Insert -- Continuation of application No. PCT/US2011/046742, filed August 5, 2011. --

Signed and Sealed this
Ninth Day of September, 2014

Michelle K. Lee
*Deputy Director of the United States Patent and Trademark Office*